United States Patent
Kimura

(10) Patent No.: US 6,331,074 B1
(45) Date of Patent: *Dec. 18, 2001

(54) THERMAL ANALYZER AND A METHOD OF MEASURING WITH THE SAME

(75) Inventor: Mitsuteru Kimura, Miyagi-gun (JP)

(73) Assignee: Ricoh Company, Ltd., Tokyo (JP); a part interest ( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/008,081

(22) Filed: Jan. 16, 1998

(30) Foreign Application Priority Data

Jan. 17, 1997 (JP) .................................................. 9-007070
Feb. 18, 1997 (JP) .................................................. 9-034077

(51) Int. Cl.[7] ............................................... G01N 25/00
(52) U.S. Cl. ............................... 374/10; 374/31; 219/209
(58) Field of Search ................... 374/10, 11, 15, 374/31, 12; 219/209, 505; 338/22 R; 73/15; 62/3.7

(56) References Cited

U.S. PATENT DOCUMENTS

| | | | |
|---|---|---|---|
| 3,773,964 | * 11/1973 | Brady et al. | 374/10 |
| 3,981,175 | * 9/1976 | Hammond, III et al. | 73/15 |
| 4,149,401 | * 4/1979 | Hentze | 73/15 |
| 4,154,085 | * 5/1979 | Hentze | 73/15 |
| 4,354,764 | * 10/1982 | Achermann et al. | 374/56 |
| 4,677,416 | * 6/1987 | Nishimoto et al. | 374/10 |
| 4,812,051 | * 3/1989 | Paulik et al. | 374/10 |
| 5,013,159 | * 5/1991 | Nakamura et al. | 374/12 |
| 5,165,732 | * 11/1992 | Townsend | 285/226 |
| 5,193,910 | * 3/1993 | Kinoshita | 374/11 |
| 5,251,980 | * 10/1993 | Hiraoka et al. | 374/7 |
| 5,288,147 | * 2/1994 | Schaefer et al. | 374/10 |
| 5,463,277 | * 10/1995 | Kimura et al. | 315/169.1 |
| 5,560,711 | * 10/1996 | Bu | 374/109 |
| 5,603,220 | * 2/1997 | Seaman | 62/3.7 |
| 5,707,148 | * 1/1998 | Visser et al. | 374/31 |
| 5,711,604 | * 1/1998 | Nakamura | 374/10 |
| 5,788,373 | * 8/1998 | Huetter et al. | 374/10 |
| 5,798,684 | * 9/1998 | Endo et al. | 338/22 R |
| 5,813,764 | * 9/1998 | Visser et al. | 374/10 |
| 6,046,433 | * 4/2000 | Gross et al. | 219/209 |

FOREIGN PATENT DOCUMENTS

534424 A1 * 9/1992 (JP) .
664554 A1 * 1/1995 (JP) .

OTHER PUBLICATIONS

Hodgson, A comprehensive thermal analysis apparatus, Journal of Scientific Instruments, pp. 61–65, Feb. 1963.*
Perkin–Elmer, Differential Scanning Calorimetry, Apr. 5, 1993.*

* cited by examiner

Primary Examiner—John Barlow
Assistant Examiner—Maria Fernandez
(74) Attorney, Agent, or Firm—Olbon, Spivak, McClelland, Maier & Neustadt, P.C.

(57) ABSTRACT

A thermal analyzer scans temperature by thermally altering a sample and measuring a thermal change based on physical and chemical changes of the sample as a function of time and/or temperature. The thermal analyzer includes a heat-generating section for heating a sample. The heat-generating section includes a first semiconductor substrate of a first conductivity type forming a thin-film heater with a cavity section in a lower section thereof and a second semiconductor substrate of a second conductivity type connected to the first substrate. The cavity section forms a sample holding section for holding the sample. The thermal analyzer further includes a temperature detecting section for detecting a temperature of the sample holding section. The sample holding section and the temperature detecting section are monolithically formed on the thin-film heater or an area proximate the thin-film heater in a thin-film supporting section for supporting the thin-film heater.

27 Claims, 17 Drawing Sheets

THERMAL ANALYZER AND A METHOD OF MEASURING WITH THE SAME

FIELD OF THE INVENTION

The present invention relates to a thermal analyzer used for examination of physical and chemical states in relation to heat of substance as well as to a method of measuring with the same, and more specifically to a thermal analyzer which can obtain information such as a melting point of an extremely minute quantity of substance, a transmit temperature, change in mass of the substance, a boiling point, specific heat types and quantities of contained substances, thermal change or change in mass associated with a chemical reaction, and a method of measuring with the same.

BACKGROUND OF THE INVENTION

As a thermal analyzer based on the conventional technology, there is, for instance, a differential thermal analyzer, or a differential scan calorimeter (DSC) based on the compensation system. The differential thermal analyzer is an apparatus which measures and records temperature difference as a function of time or temperature between a substance as an object for thermal analysis and a reference substance both put under conditions for heating or cooling the samples at an adjusted rate.

The differential scan calorimeter based on the compensation system compensates for a temperature difference between a sample to be measured and a reference substance with a heater of a compensating circuit, and records the compensation rate (difference in an energy supply rate).

Further as a thermal analyzer based on the conventional technology, there is an apparatus which uses a magnetic balance and detects changes in magnetized rate based on transmit temperature such as the Curie temperature, when scanning temperature of a magnetic body, by detecting a force in and inhomogeneous magnetic field; or an apparatus like vibrating sample type of magnetometer (VSM) which vibrates a sample magnetized with a magnet at a low frequency and detects changes of a magnetic field caused by change of a space with a magnetism sensor such as a coil to detect change of change in magnetized rate at transmit temperature such as Curie temperature when scanning temperature.

However, with the thermal analyzers based on the conventional technology as described above, efforts for size reduction can be recognized in each of the apparatus, but the apparatuses have the configuration in which heaters each manufactured independently are arrayed, so that the total quantity of heat generated by these heaters is large with the response rather dull and for this reason there is no way but to increase a quantity of sample to be measured, and in addition each heater requires a large power, and when high temperature such as several hundred degrees is required, it is difficult to shield the generated heat, and because of this problem, the size of each apparatus inevitably becomes larger, and further it is disadvantageously difficult to achieve homogeneity in temperature, and also it is difficult to equalize characteristics of a heater for a sample to be measured to those of a heater for a standard sample.

Also as for a thermocouple or a thermopile as a temperature sensor for detecting temperature, those independently manufactured are inserted and contacted to each other, and size of each apparatus based on the conventional technology inevitably becomes larger for considerations to a problem of thermal contact, the problems concerning size of each component, and the necessity for a wiring space, and as a result the cost of each apparatus becomes very expensive.

Also the conventional type of thermal analyzers each based on a magnetic body such as a magnetic balance or a VSM have problems such as that the size is large, or that a magnet having a large size is required for raising the detection sensitivity as amplitude of a magnetic field becomes abruptly smaller when it gets away from a magnetic pole.

SUMMARY OF THE INVENTION

It is an object of the present invention to provide a thermal analyzer which enables measurement with an extremely small quantity of sample by heating the sample with a heater having an extremely small heat capacity and can heat the sample with a minute current up to high temperature with a high response speed, and further which can be produced in mass with the unified specifications.

It is another object of the present invention to provide a thermal analyzer which enables a high speed response with a minute current.

The thermal analyzer according to the present invention scans temperature by thermally altering a sample and measuring a thermal change based on physical and chemical changes of the sample as a function of time and/or temperature. The thermal analyzer includes a heat-generating section for heating a sample. The heat-generating section includes a first semiconductor substrate of a first conductivity type forming a thin-film heater with a cavity section in a lower section thereof and a second semiconductor substrate of a second conductivity type connected to the first substrate. The cavity section forms a sample holding section for holding the sample. The thermal analyzer further includes a temperature detecting section for detecting a temperature of the sample holding section. The sample holding section and the temperature detecting section are monolithically formed on the thin-film heater or an area proximate the thin-film heater in a thin-film supporting section for supporting the thin-film heater.

In the measuring method with a thermal analyzer according to the present invention, when temperature scanning is executed with the thermal analyzer by letting a current flow through a thin-film heater, a current component for heating or cooling a sample at a constant rate is superimposed over an AC current component for minutely changing temperature, and a temperature change component corresponding to the AC current component is taken out as a signal from the temperature detecting unit; and the signal is subjected to a prespecified processing, and for that purpose the thermal analyzer according to the above invention has a high responsibility, so that a current component for heating or cooling a sample at a constant rate can be superimposed over an AC current component for minutely changing temperature. In other words, the measuring method with a thermal analyzer having a high responsibility even at a minute power can be provided.

Other objects and features of this invention will become understood from the following description with reference to the accompanying drawings.

DESCRIPTION OF THE PREFERRED EMBODIMENTS

Next detailed description is made for embodiments of a thermal analyzer according to the present invention as well as a method of measuring with the analyzer with reference to the drawings.

Figure 1:
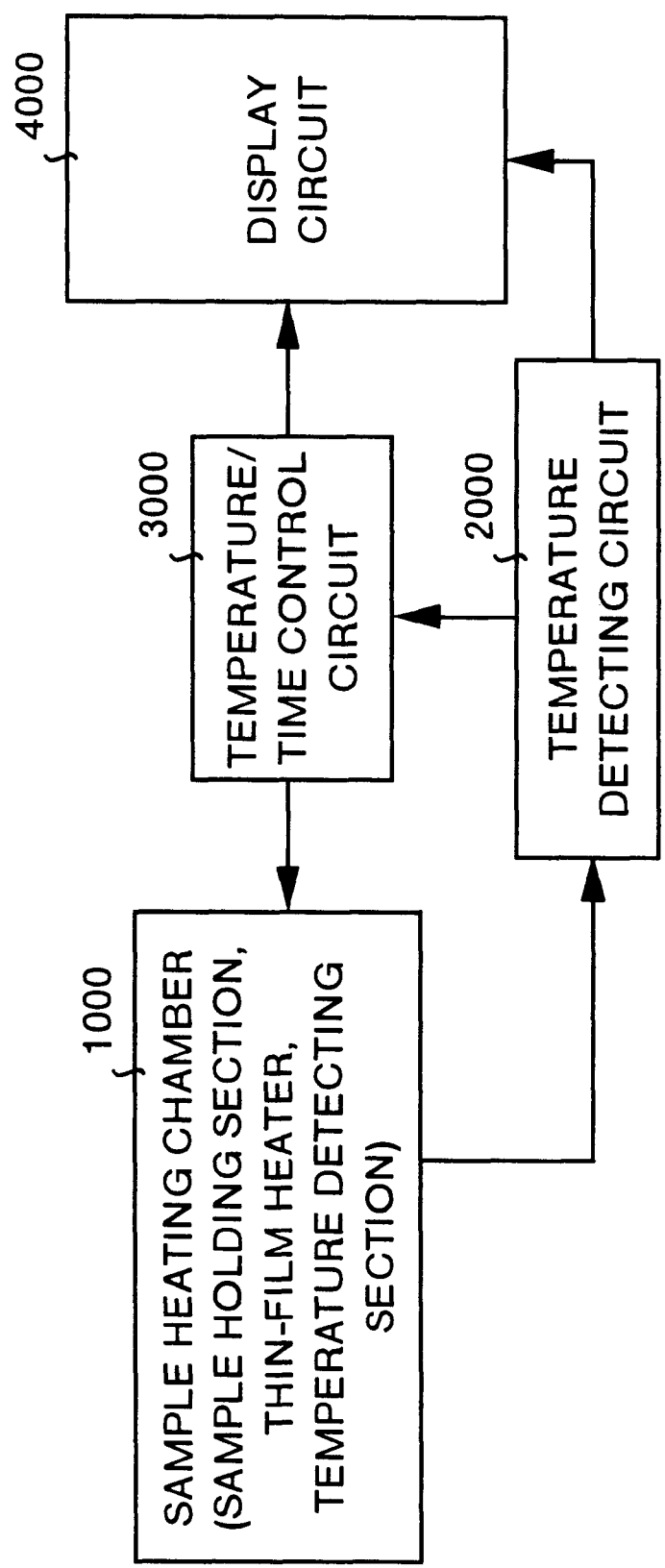
FIG. 1 is a general block diagram showing a thermal analyzer according to the present invention.

FIG. 1 is a general block diagram showing a thermal analyzer according to the present invention. The thermal analyzer comprises a sample heating chamber 1000, a temperature detecting circuit 2000, a temperature/time control circuit 3000, and a display circuit 4000.

Accommodated in the sample heating chamber 1000 are a thin-film as a heat-generating section (a heating/cooling unit) monolithically formed on a substrate, a thin-film supporting section on the thin-film heater, a sample holding section formed on the thin-film heater or in an area close to said thin-film supporting section, and a temperature detecting section for measuring temperature of the sample holding section. It should be noted that a signal outputted from this temperature detecting section is processed in the temperature detecting circuit 2000, a portion of a signal therefrom is sent to the temperature/time control circuit 3000, determined and processed therein, and a portion thereof is returned as a signal for temperature scanning to the sample heating chamber 1000 and used for scanning the temperature of the thin-film heater.

Also, a portion of a signal from the temperature detecting circuit 2000 and the temperature/time control circuit 3000 is sent to the display circuit 4000 and is used and displayed as a signal for display relating to various kinds of temperatures.

Figure 2:
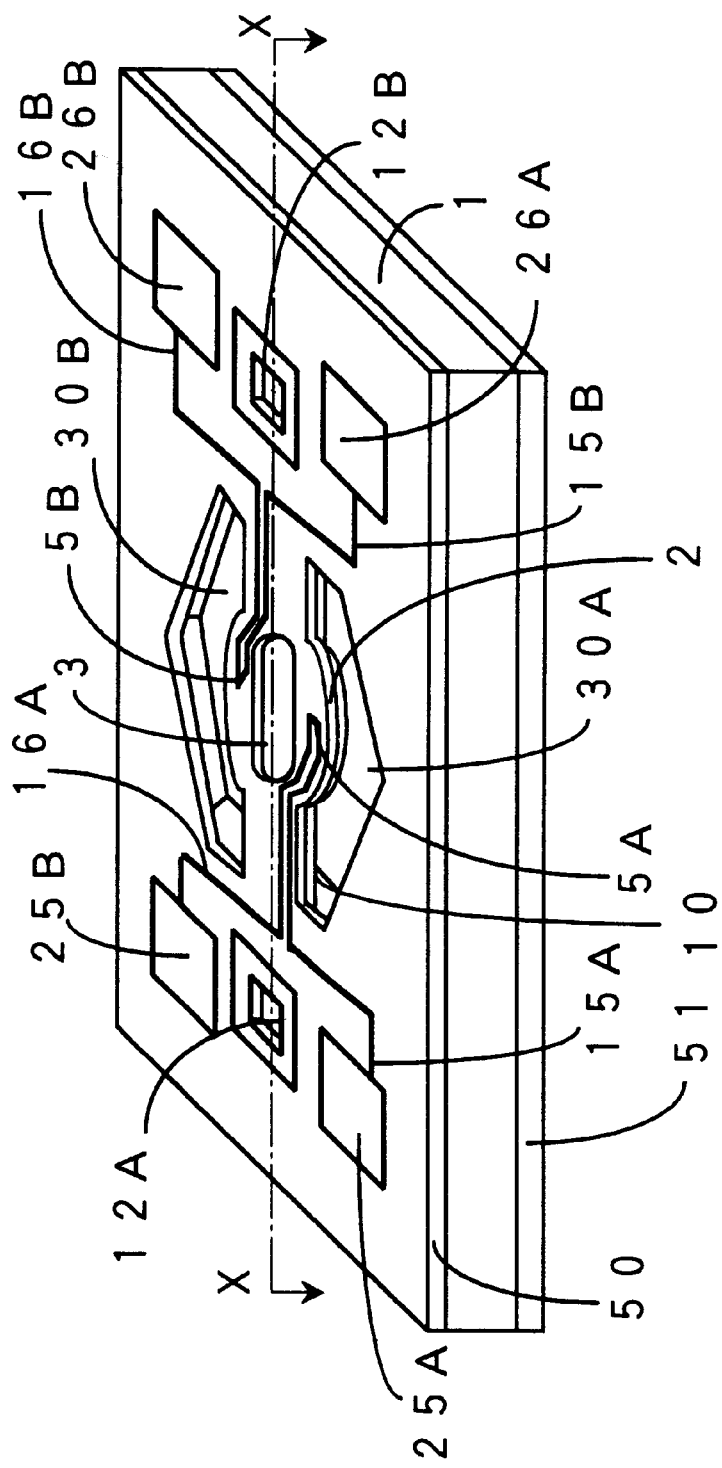
FIG. 2 is a general perspective view showing one embodiment of a substrate with a sample heating chamber provided thereon in the thermal analyzer according to the present invention.
Figure 3:
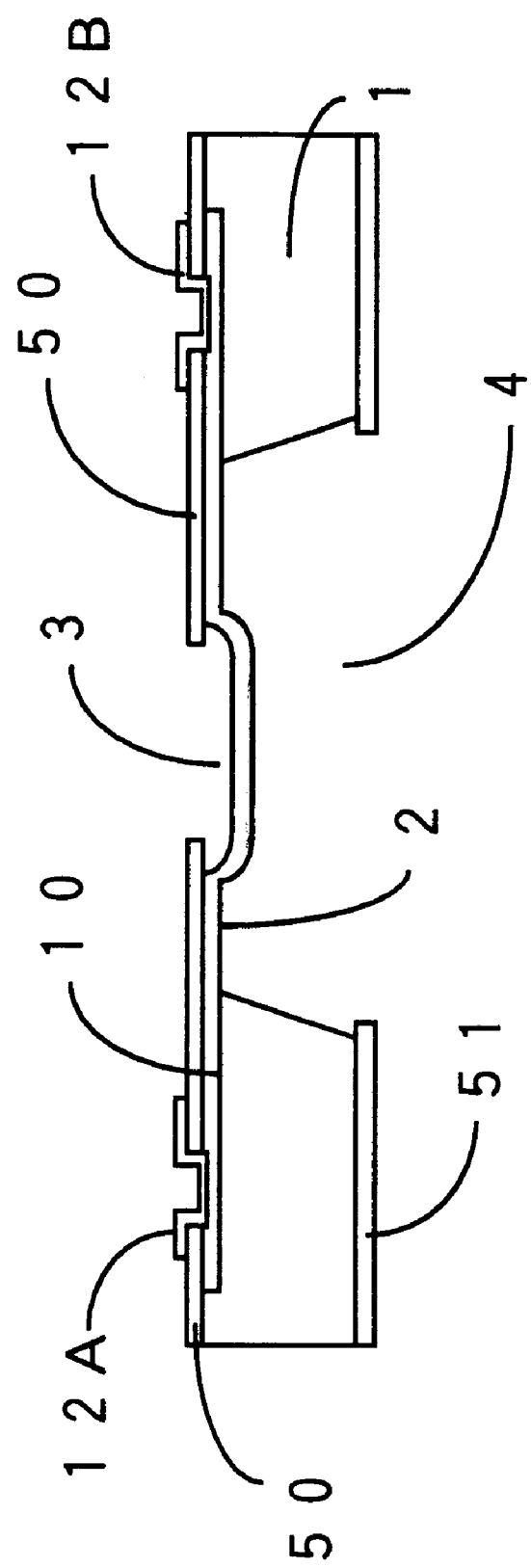
FIG. 3 is a cross-sectional view taken along the line X—X in the perspective view shown in FIG. 2.

FIG. 2 is a general perspective view showing one embodiment of a substrate with a sample heating chamber or other components provided thereon in the thermal analyzer according to the present invention, and FIG. 3 is a cross-section taken along the line X—X in the general perspective view shown in FIG. 2. The sample heating chamber according to this embodiment shows a case where a sample holding section 3 is formed directly on one piece of a thin-film heater.

The substrate 1 with the sample heating chamber or other components provided thereon can be formed, for instance, in the following way.

At first, using a n-type monochrystal silicon substrate with the (100) surface upside, and with the known photolithography technology, a cavity as the sample holding section 3 is formed into an oval form with, for instance, width of 200 $\mu$m, length of 400 $\mu$m, and depth of 20 $\mu$m by means of isotropic etchant. Then an $SiO_2$ film with the thickness of around 1 $\mu$m is formed on the entire surface by means of thermal oxidization, a window with a desired pattern is formed to form a thin-film heater 2 on one surface thereof, and an impurity diffusion layer 10 with the depth of around 4 μm is formed with high density boron at the density of $2 \times 10^{20}$ cm-3 or more on the exposed silicon substrate surface to form the thin-film heater 2 as a heat-generating section.

Then the $SiO_2$ film on the entire surface of the silicon substrate is removed by means of etching, and then in a case of a thermally oxidized $SiO_2$ film, that with the thickness of around 0.3 μm because the thermal expansion coefficient is largely different from that of silicon, and in a case of oxynitelide thin-film, that with the thickness of around 1 μm is formed because a thick film is allowable in that case, and the films are used as electrically insulating thin-films 50, 51 also available as thin-films for anisotropic etch mask to form the cavity section 4.

Then thermocouple 15A, 16A, 15B, 16B as temperature detecting sections 5A, 5B are formed in vicinity of the sample holding section 3 to measure temperature of the sample holding section 3 at two places and guess the temperature of the sample holding section 3 from the average value.

As these thermocouples 15A, 16A, 15B, 16B, for instance, a combination of gold (Au) and nickel (Ni) may be used. It is more convenient to use a combination of metallic thermocouples each with high durability for an etchant for anisotropic etching to form the cavity section 4.

As electrodes 25A, 26A, 25B, 26B of the thermocouple, materials of the thermocouple may be used as they are. As Au is easily separated from the $SiO_2$ film, it is desirable to form a titanium (Ti) layer with the thickness of around 0.01 μm as an adhering layer on an interface between the two materials.

Then windows for forming the electrodes 12A, 12B for the thin-film heater 2 are formed on the electrically insulating thin-films 50, 51, and for instance, nickel (Ni) is sputtered into desired patterns each with the thickness of around 0.3 μm as the electrode 12A, 12B. It should be noted that the windows for forming the electrodes 12A, 12B may be formed prior to formation of the thermocouple and the electrodes 12A, 12B for the thin-film heater 2 may be formed simultaneously when the nickel (Ni) film in the thermocouple is formed.

Then windows positionally aligned are formed on a rear surface as well as of a top surface of the electrically insulating thin-films 51, 50 so that holes 30A, 30B are formed at the window sections formed on the upper electrically insulating thin-film 50 and also the thin-film heater 2 based on a bridge structure and having a specified size is formed when the cavity section 4 is formed under the thin-film heater 2 by executing anisotropic etching to the silicon substrate.

It should be noted that, in this case, as the impurity diffusion layer 10 has been formed with high density boron with the density of $2 \times 10^{20}$ cm$^{-3}$ or more in this bridge-structured thin-film heater 2, the thin-film heater 2 little reacts to an anisotropic etching solution such as hydrazine and remains as it is. Also as n-type silicon is used as the substrate 1, the thin-film heater 2 as a heat-generating section is of p-type because boron is added thereto, so that a pn junction is formed and a current path can be limited to the thin-film heater 2 when a current flows to the electrodes 12A, 12B of the thin-film heater 2.

Figure 4:
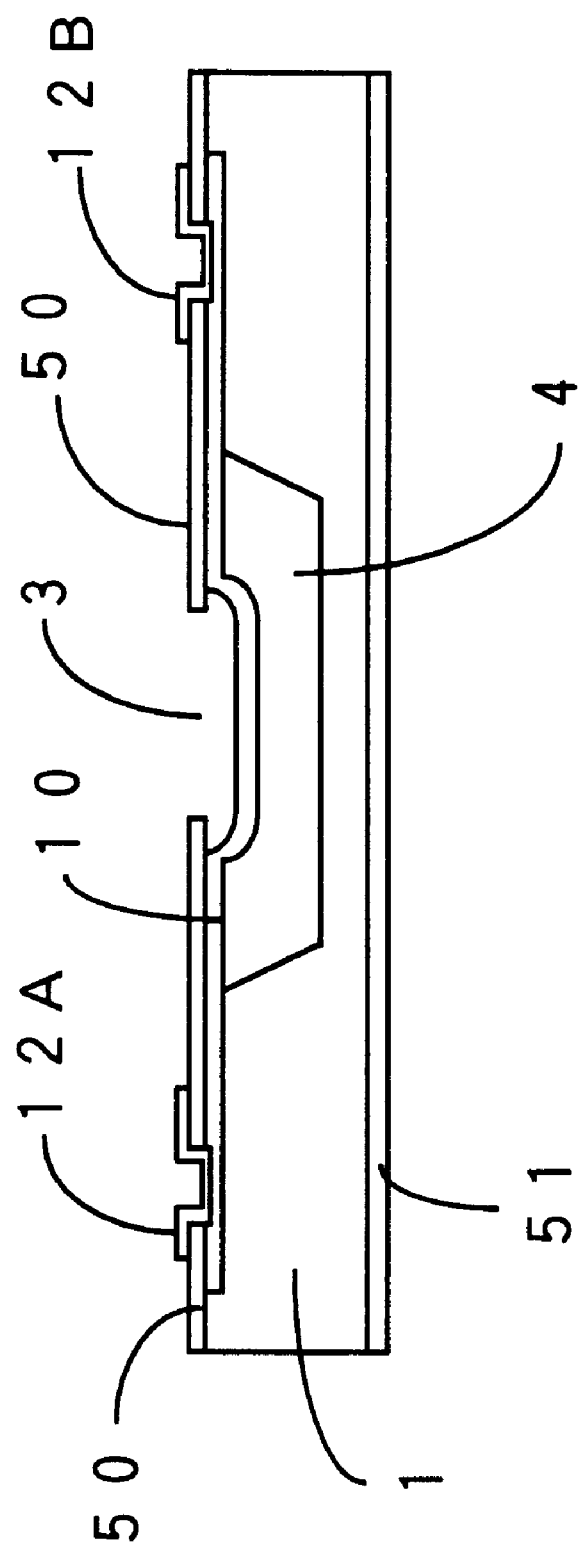
FIG. 4 is a cross-sectional view showing another embodiment of a substrate with a sample heating chamber or other components provided thereon in the thermal analyzer according to the present invention.

FIG. 4 shows a case where formation of the cavity section 4 in the substrate with a sample heating chamber or other components provided thereon in the thermal analyzer according to the present invention as shown in FIG. 2 and FIG. 3 above is executed only through the windows formed on the upper electrically insulating film 50 by means of etching the substrate silicon.

FIG. 4 shows a case where the cavity section 4 formed by anisotropic etching from a top surface of the substrate 1 does not reach a bottom of the substrate due to shortage of the etching time, and the cavity section 4 reaching the rear surface of the substrate 1 may be formed by adjusting dimension of the top surface of the substrate 1 or the etching time.

When a penetrating cavity section reaching a bottom of the substrate 1 is formed as described above, dimensions of the cavity section 4 become larger, and also a hole is opened on the bottom surface of the substrate 1, and a liquidous sample spilled from the sample holding section 3 fills the cavity section 4, which advantageously eliminates the possibility of prevention of temperature increase in the thin-film heater 2.

Figure 5:
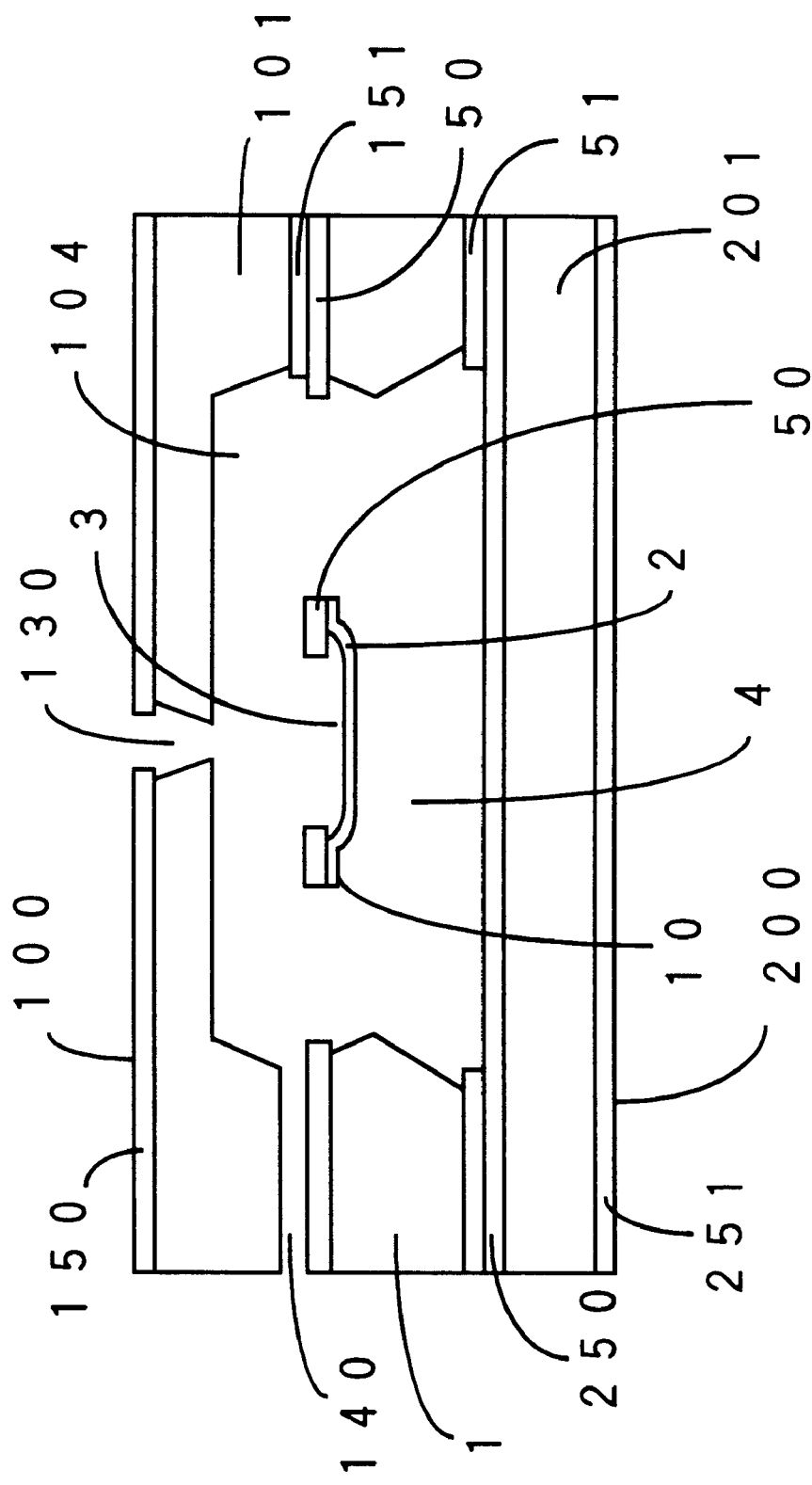
FIG. 5 is a cross-sectional view showing one embodiment of a structure of a basic body of a thermally analyzing section in the thermal analyzer according to the present invention.

FIG. 5 is a cross-sectional view showing one embodiment of a structure of a basic body of a thermally analyzing section in which a cover 100 is jointed to the substrate 1 with a sample heating chamber or other components provided thereon in the thermal analyzer according to the present invention shown in FIG. 2 and FIG. 3 and further a cover 200 is jointed to a rear surface of the substrate 1. A substrate 101 of the cover 100 is made from monochrystaline silicon, and a cavity section 104 with high precision is provided by anisotropically etching silicon in a section contacting an upper section of the thin-film heater 2 on this upper cove 100, and further a hole 130 formed with high precision by anisotropically etching silicon is formed at a position just above the sample holding section 3, and this hole 130 also functions as a measure for a liquidous sample or a powder sample.

Further a slender groove 140 is formed with high precision also by anisotropically etching silicon on this upper cover 100, and when air or other gas in the cavity section 104 as well as in the cavity section 4 is sucked through this groove 140 and a negative pressure is realized in the cavity sections, a sample filling the hole 130 slowly drops into the sample holding section 3, so that a specified quantity of sample can be put into the sample holding section 3. When the thermally oxidized $SiO_2$ film is used as the electrically insulating thin-film 150, 151, the thin-film can also be used as a mask for anisotropically etching silicon, which is convenient. Also it is advisable to use a silicon substrate 201 for the lower cover 200 and thermally oxidized $SiO_2$ film for the electrically insulating thin-films 250, 251.

In the embodiment shown in FIG. 5, monocrystaline silicon is used as a material for all of the substrate 1, cover 100, and cover 200, but other material may be used on the condition that a precise precision can be obtained. For instance, a non-crystalline material such as a glass substrate may be used for the cover 200. As a material for these covers, it is better to select one having a thermal expansion coefficient close that of the substrate 1 adjoining the substrates.

Figure 6:
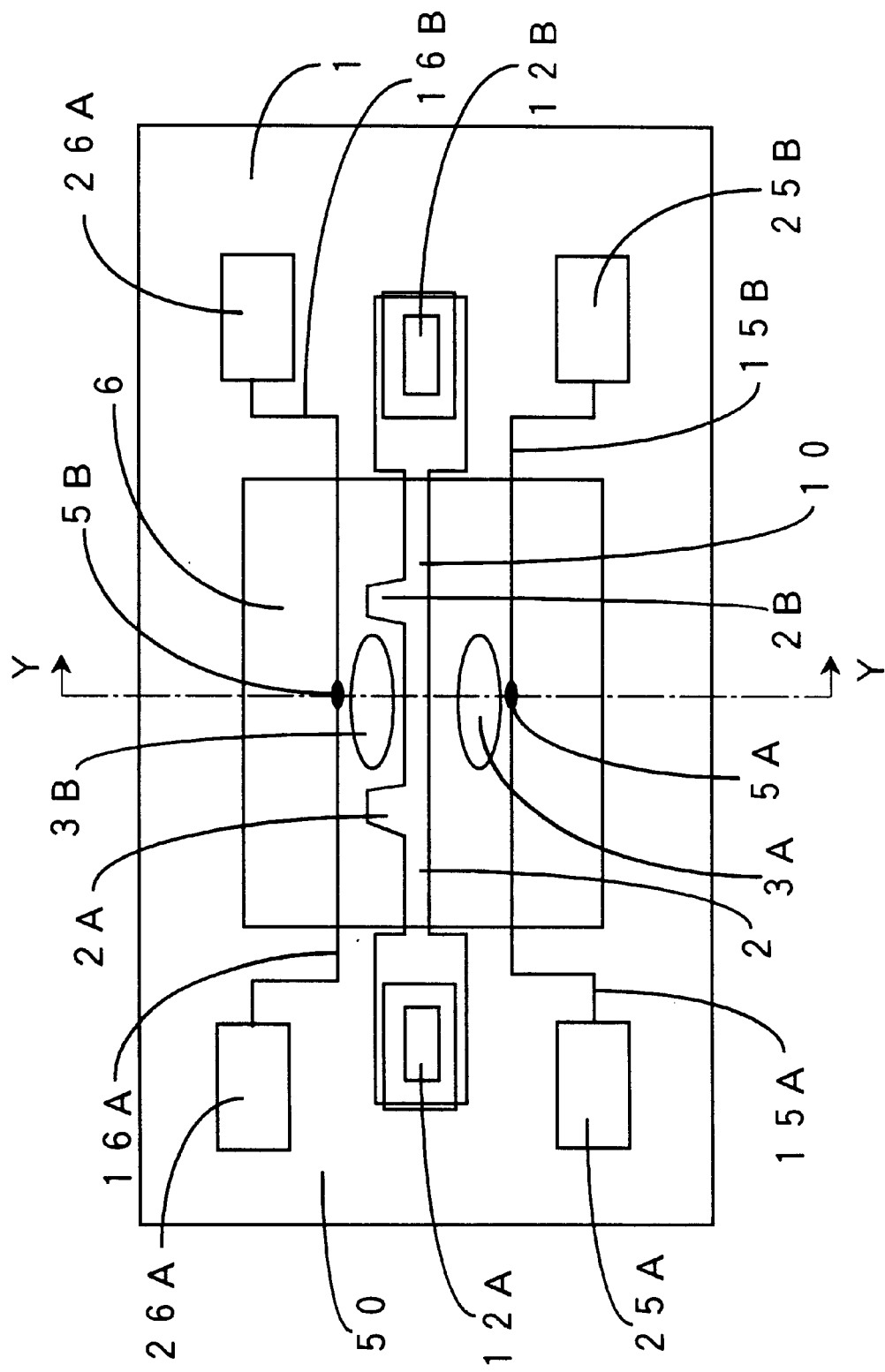
FIG. 6 is a general perspective view showing one embodiment of a substrate with a sample heating chamber or other components provided thereon in the thermal analyzer according to the present invention.

FIG. 6 shows another embodiment of the substrate 1 with a sample heating chamber or other components provided thereon in the thermal analyzer according to the present invention, and in this case two sample holding sections 3A, 3B are formed on a thin-film supporting section 6 for supporting the thin-film heater 2, and in addition the thin-film supporting section 6 is based on the diaphragm structure, and the thin-film heater 2 is slenderly adhered in one way to a section around a center of this thin-film supporting section 6.

Herein thin-film heaters 2A, 2B for additionally heating to realize asymmetricity in the thin-film heater 2 so that temperature of the sample holding section 3B, which is one of the two units of sample holding sections 3A, 3B, will become slightly higher as compared to that of the remaining sample holding section 3A under the same conditions. In the thermal analyzer according to the present invention having the configuration as described above, even if the same sample is put in two sample holding sections 3A, 3B, the sample holding section 3B is heated first up to, for instance, a melting point Tm of the sample, while temperature of the sample in the sample holding section 3A is still lower as compared to the melting point Tm, and a temperature difference ΔT between temperature of the sample holding section 3A and that of the sample holding section 3B measured with temperature detecting sections 5A, 5B provided in vicinity of the sampling holding sections 3A, 3B functions like a differential value of temperature increase as a function of elapse of time.

For this reason, even if the same sample is put in the two sample holding sections, the sample put in another sample holding section functions as a standard sample. Also when temperature of the sample in the sample holding section 3A with lower temperature reaches the melting point of the sample, a waveform for time t—temperature difference ΔT in the reverse form is observed. The monitoring precision can be improved by making use of these waveforms.

Figure 7:
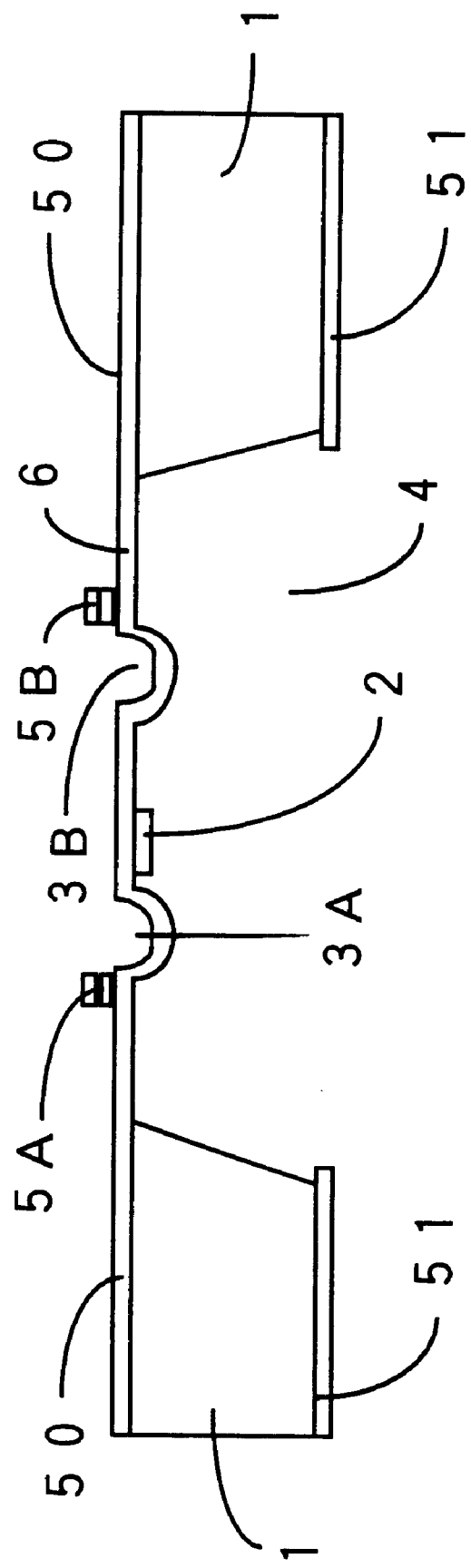
FIG. 7 is a cross-sectional view of a substrate 1 with a sample heating chamber or other components provided therein in the thermal analyzer according to the embodiment taken along the line Y—Y in FIG. 6.

FIG. 7 is a cross-sectional view showing the substrate 1 with a sample heating chamber or other components provided thereon according to the embodiment shown in FIG. 6 taken along the line Y—Y. The method of forming the substrate 1 with a sample heating chamber or other components provided thereon according to the embodiment shown in FIG. 6 and FIG. 7 is the same as that according to FIG. 2 and FIG. 3, so that description thereof is omitted herein.

Figure 8:
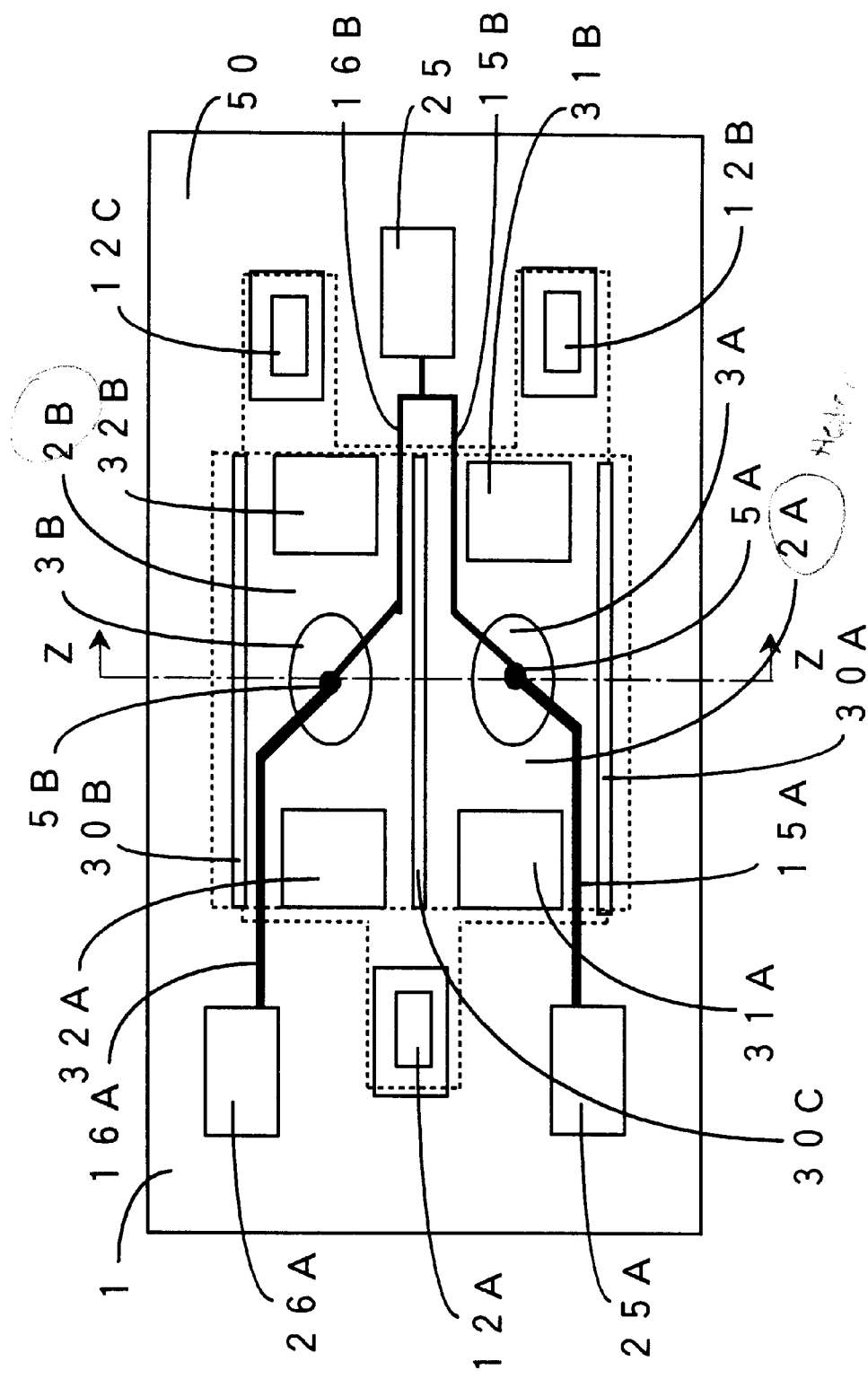
FIG. 8 is a view showing another embodiment of the substrate 1 with a sample heating chamber or other components provided thereon in the thermal analyzer according to the present invention.

FIG. 8 shows another embodiment of the substrate with a sample heating chamber or other components provided thereon in the thermal analyzer according to the present invention. When the thin-film heater 2 or the thin-film supporting section 6 is based on the diaphragm structure as shown in FIG. 6, power consumption becomes larger due to heat conduction to the substrate. For this reason, to overcome this defect, herein slit-formed holes 30A, 30B, 30C are formed in the diaphragm and holes 31A, 31B, 31C are provided in a supporting section for the thin-film heater 2, and further two thin-film heaters 2A, 2B are formed in correspondence to the two sample holding sections 3A, 3B, and temperature detecting sections 5A, 5B are formed at bottoms of the cavities of the sample holding sections 3A, 3B to detect temperature of the two sample holding sections 3A, 3B with high precision.

Only three electrodes 12A, 12B, 12C are provided as electrodes for the two thin-film heaters 2A, 2B. Further temperature detecting sections 5A, 5B for detecting a temperature difference between the two sample holding sections 3A, 3B are formed with thermocouples 15A, 15B and thermocouples 16A, 16B, and wiring is provided so that only the electrode 25, 25A, 25B are used as terminals for these thermocouples. In this step, temperature of the sample holding section 3A as a reference can be detected according to an electromotive force of the thermocouples 15A, 15B between the electrode 25 and electrode 25A.

A sample to be measured and a standard sample are put in the two sample holding sections 3A, 3B respectively to detect a temperature difference ΔT, the absolute temperature is measured, and further weights of the samples are measured, so that various physical characteristics relating to temperature of the sample to be measured can be measured like in the thermal analyzer based on the conventional technology.

Figure 9:
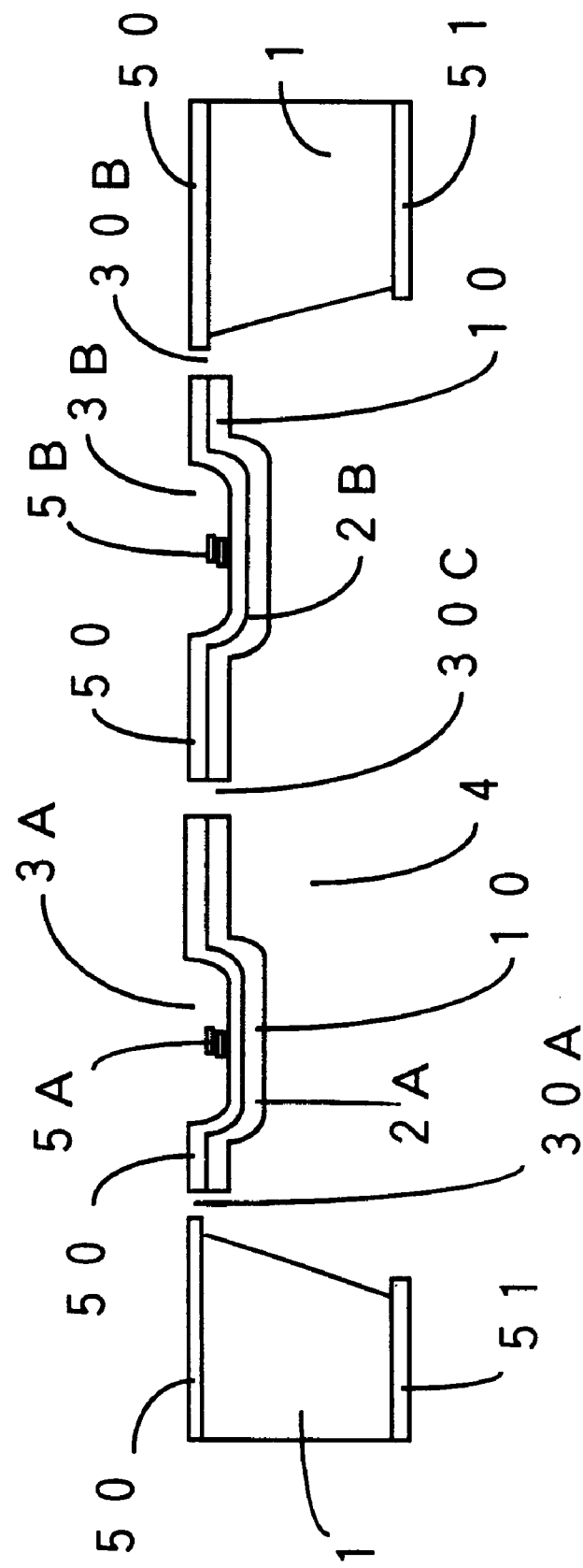
FIG. 9 is a cross-sectional view of the substrate 1 with a sample heating chamber or other components provided thereon according to the embodiment taken along the line Z—Z shown in FIG. 8.

FIG. 9 is a cross-sectional view showing the substrate 1 with a sample heating chamber or other components provided thereon according to the embodiment shown in FIG. 8 taken along the line Z—Z in FIG. 8. Also in this embodiment, as shown in the embodiment described above, the thin-film heaters 2A, 2B comprise the impurity diffusion layer 10 made from high density boron. The method of preparing the layer 10 is the same as that in the embodiment described above, so that description for the manufacturing method is omitted herein.

Also in the embodiment described above, a case where the impurity diffusion layer 10 made from high density boron is used as the thin-film heater 2 was described, but any type of thin-film heater is allowable, and for instance, a thin-film heater obtained by forming a sputtering platinum thin-film often used in the art or a nichrome thin-film into a jig-zag form may be used as the thin-film supporting section.

Although no description was made in relation to the embodiment described above, it is convenient to form a thin-film form of platinum resistor or a thermistor on the substrate 1 to know the absolute temperature of the substrate 1.

Also no description was made in relation to the embodiment described above, but three sample holding sections 3 may be prepared with one of them kept empty, while a sample to be measured and a standard sample are put in other two sample holding sections to measure thermal properties of the sample to be measured with high precision from the temperature relation between the two samples.

Figure 10:
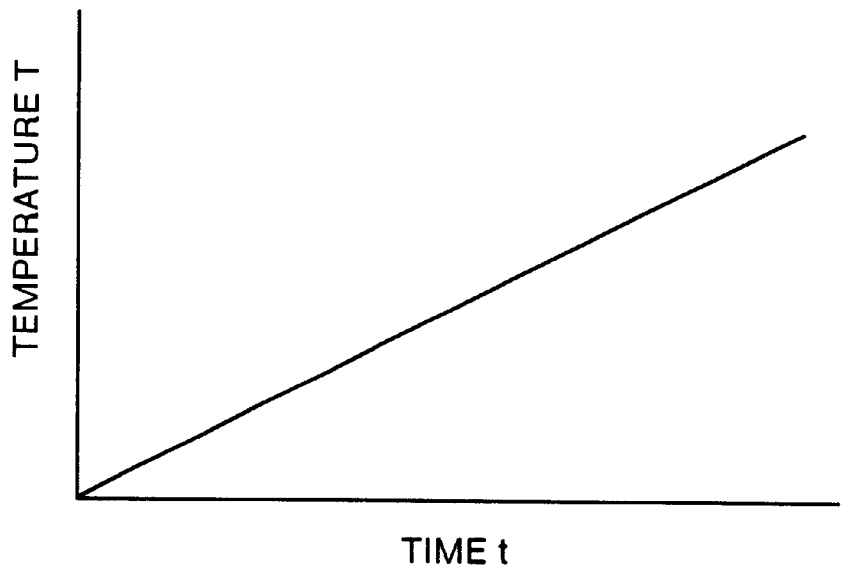
FIG. 10 is a graph showing time t and temperature T in a case where temperature scanning is executed for a certain period of time at a constant speed in a sample heating chamber in the thermal analyzer according to the present invention.

Usually temperature scanning is executed at a constant speed against time, as shown in FIG. 10, in the sample heating chamber in the thermal analyzer according to the present invention. For instance, the thin-film heater 2 with the length of 2000 μm, width of 700 μm, and thickness of around 4 μm based on a bridge structure and formed by means of thermal dispersion of high density boron has a resistance value of around 10Ω, and in the state where a loaded voltage is several V and no sample is put in, temperature of the sample holding section goes up even to several hundred degrees centigrade.

Although a temperature scanning speed of the thin-film heater 2 may be raised at a constant rate against time and according to a voltage or a current, and in that case, the temperature does not go up at a constant rate, and rather rises according to a curve for square of time. To convert the rate to a constant temperature increase rate, as shown in the general block diagram showing the general configuration of the present invention in FIG. 1, a temperature output signal from the temperature detecting section 5 for measuring temperature of the sample holding section 3 may be processed with a microcomputer, and a signal from the microcomputer may be returned to a driving source for the thin-film heater 2 to control the temperature. It is also possible to convert the temperature scanning speed to a desired temperature raising rate or a desired temperature falling speed by processing the temperature output signal with the microcomputer. It is needless to say that it is possible to provide temperature control so that a difference in temperature between the sample to be measured and the standard temperature is eliminated or to intermittently let a current flow and measure the heat/time index or change thereof.

Figure 11:
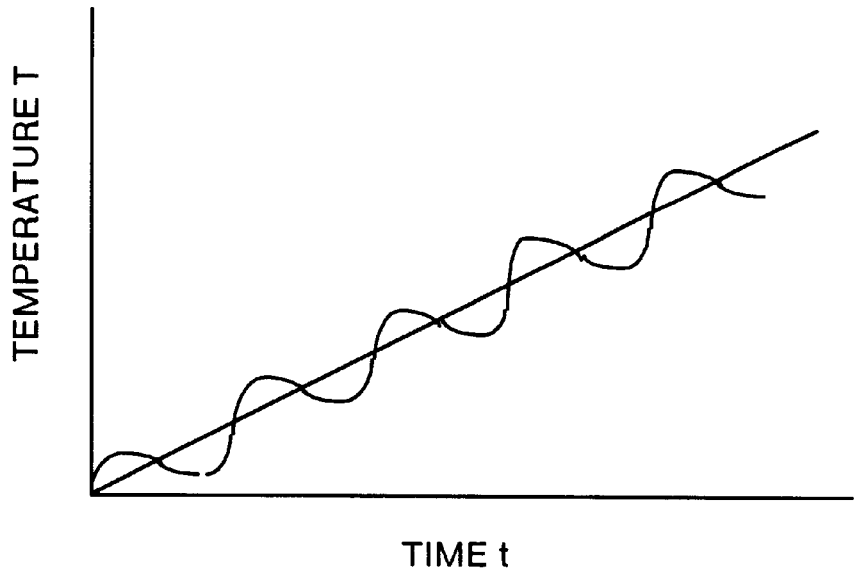
FIG. 11 is a graph showing time t and temperature T in a case where temperature change is given to a sample holding section by superimposing a minute AD current when scanning temperature for a certain period of time at a constant speed in a sample heating chamber in the thermal analyzer according to the present invention.

As a thin-film heater having an extremely small heat capacity is used in the sample heating chamber in the thermal analyzer according to the present invention, the heat/time index is very small; for instance, 10 milliseconds, so that an extremely small quantity of sample can be measured within a short period of time. For instance, to raise temperature of a sample to around 100° C., only around 1 second is required. With the characteristics as described above, temperature scanning is executed at a constant rate against time, but as shown in FIG. 11, the same effect as indicated by a differential waveform for temperature when temperature is rising or falling can be achieved by superimposing a minute AC current with a frequency of several hertz to cause minute change of temperature and detecting and processing the temperature change component in synchronism to this AC current for display.

Figure 12:
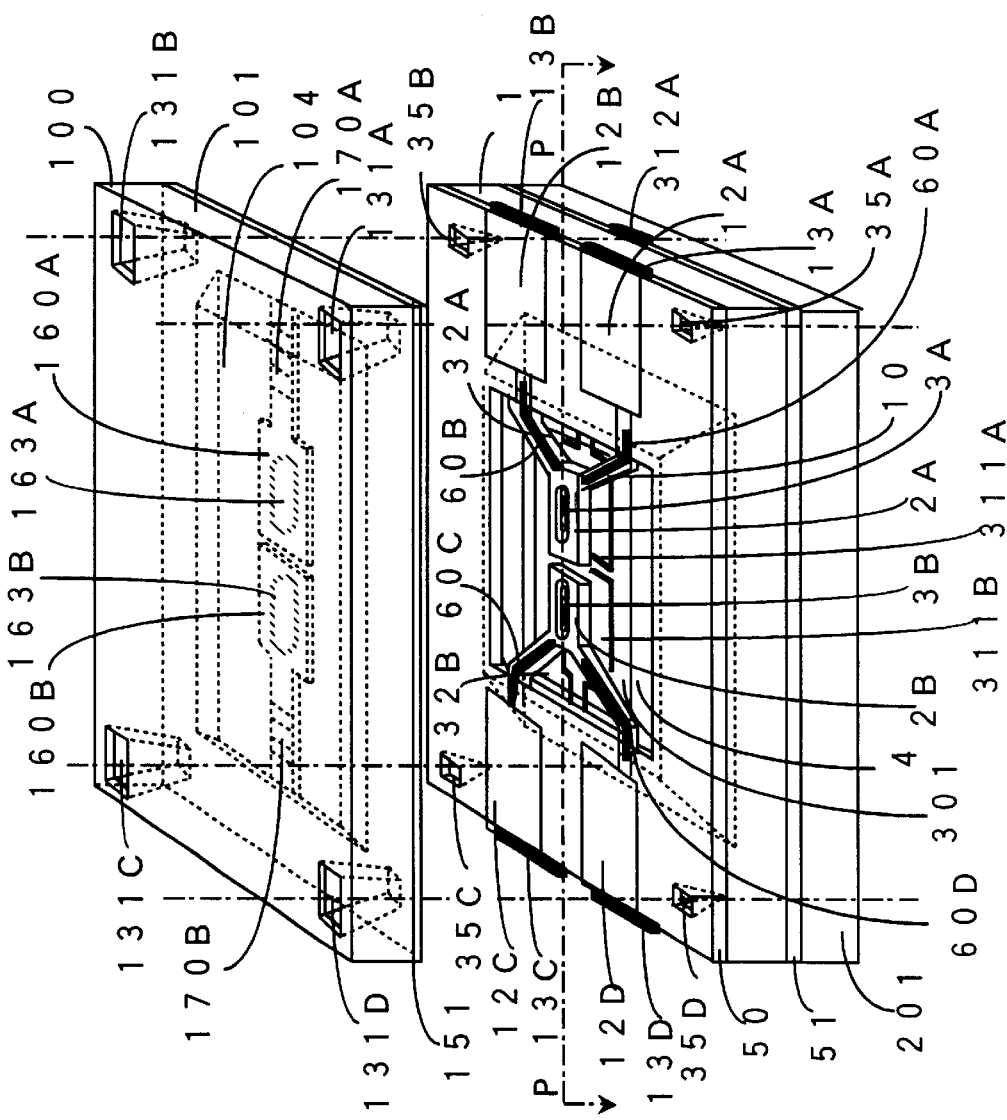
FIG. 12 is a general view showing an embodiment of the present invention in which an electrostatic capacity is used as a means for exciting vibration so that a sample holding section formed on a canti-lever type of thin-film heater in the thermal analyzer according to the present invention can be vibrated.

FIG. 12 is a general block diagram showing an embodiment of the present invention in which electrostatic capacities formed with thin-film heaters 2A, 2B and fixed electrodes 311A, 311B and functioning as an exciting unit and a vibration detecting unit respectively are used so that the sample holding sections 3 formed in the canti-lever type of thin-film heaters 2A, 2B in the thermal analyzer according to the present invention are vibrated. It should be noted that the temperature detecting section and electrodes thereof are omitted in the figure of this embodiment to evade complexity.

When an AC voltage is loaded to the electrostatic capacities formed with the thin-film heaters 2A, 2B and fixed electrodes 311A, 311B respectively, the sample holding sections 3A, 3B formed on the thin-film heaters 2A, 2B are attracted by an electrostatic sucking force to the fixed electrodes 311A, 311B and start vibration. As the electrostatic capacity is larger, the electrostatic sucking force becomes larger, so that the fixed electrodes 311A, 311B should preferably be placed at positions close to the thin-film heaters 2A, 2B respectively provided that the fixed electrodes do not impede vibration of the thin-film heaters 2A, 2B. For this purpose, it is advisable to place a substrate 301 having a cross-section like a trapezoid on and in close contact to the base plate 201 of the insulating body of the cover 200 to form the electrodes 311A, 311B for electrostatic capacity on these hybrid substrates.

Also, it is advisable to form each electrode in the manner that terminals 13A, 13B, 13C, 13D, 312A and 312B of electrodes are provided outside the chip by extending them outside via each contact surface between the substrate 1, substrate 101 and substrate 201.

When a resonance frequency fr when samples are inserted into the sample holding sections 3A, 3B is 2 times higher as compared to a frequency fe of the AC voltage for excitation, vibration can be excited with high efficiency. Of course, when the frequency fe of the AC current for excitation is a value obtained by dividing the resonance frequency fr by an integral number, the resonance frequency fr of the vibration system can effectively be excited. For instance, when water is put in the sample holding section 3A and then the resonance frequency fr of the cantilever type of thin-film heater 2A is 200 Hz, if an AC current with the frequency fe for excitation of 100 Hz is loaded to a section between the thin-film heater 2A and the electrode 311A for an electrostatic capacity, the thin-film heater 2A having the canti-lever type of sample holding section 3A can be excited.

Also in this step, in association with positional change of the thin-film heater 2A, the electrostatic capacity consisting of the thin-film heater 2A and the electrode 311A changes, so that, by making use of the electrostatic capacity as a vibration detecting unit, self-excited vibration can be generated by providing a known self-excited vibrating unit based on a feedback system combined with an amplifier not shown herein.

When evaporation of a sample occurs due to temperature scanning, or when a change of mass occurs due to a chemical reaction with an atmospheric gas or a chemical reaction in the mixed samples, a change of mass in the canti-lever type of vibration system of the thin-film heater 2A having the sample holding section 3A occurs, so that the resonance frequency fr changes and change of mass of the sample can be measured by detecting change in this resonance frequency fr.

Also in this embodiment, to prevent a sample from spilling from the sample holding sections 3A, 3B due to vibration, or to easily realize homogeneity of temperature in a sample by covering the sample, the thin-film covers 160A and 160B having cavities 163A, 163B are provided in a substrate 101 of the cover 100 also based on the cantilever structure. These thin-film covers 160A, 160B can easily be formed with the materials such as silicon oxide film or silicon nitride film simultaneously when a cavity section 104 is formed in the cover 100 by means of anisotropic etching.

Also irregular thin-film springs 170a, 170B are formed on the thin-film covers 160A, 160B so that these thin-film covers 160A, 160B can easily adhere to the sample holding sections 3A, 3B. Of course the thin-film covers 160A, 160B are designed so that, when the cover 100 is jointed to the substrate 1 with the sample holding sections 3A, 3B or other components provided therein, the cavities 163A, 163B of the thin-film covers 160A, 160B are just positionally aligned to the sample holding sections 3A, 3B. To easily make the positional alignment described above, it is advantageous to form V-shaped grooves 35A, 35B, 35C, 35D at four corners of a cut chip as the substrate 1 and to form through-holes 131A, 131B, 131C, and 131D on the cover 100 at positions corresponding to the grooves above. It is more advantageous to insert a pin into each of the through-holes 131A, 131B, 131C, 131D.

In this embodiment, to effectively supply an electric power to the thin-film heaters 2A, 2B, only the sample holding sections 3A, 3B or an area in vicinity thereto are designed so that heat generation hardly occurs by shortcircuiting the impurity diffusion layer 10 made from high density boron in an arm section of the cantilever, of the impurity diffusion layer 10 made from high density boron in the entire cantilever, with metal having a small electric resistance such as shortciruiting films 60A, 60B, 60C, and 60D made from gold (Au). Further, holes 32A, 32B are provided near fixed edges of the cantilever to minimize conduction of heat to the substrate 1, to make smaller an air resistance in vibration, and to prevent generation of distorted vibration.

In this embodiment, the thin-film covers 160A, 160B are provided on the substrate 101 with a cantilever shape to prevent a sample, especially in vibrating from spilling from the sample holding sections 3A, 3B due to vibration, but especially when a sample is a liquidous one, the thin-film covers 160A, 160B may have the same form as that of the cantilever shaped thin-film heaters 2, 2R, 2L having the sample holding sections 3A, 3B so that the areas around the components are closely adhered to each other when overlaid on each other, and also the cavities 163A, 163B provided in the thin-film covers 160A, 160B may be extended in a form like a slender groove up to the substrate 1 of a supporting edge of the canti-lever and to the substrate 101 for the purpose to form two tubes, so that the liquidous sample can be fed into the sample holding sections 3A, 3B through the tubes formed between the substrate 1 and the substrate 101.

Although not shown in this embodiment, a form of the sample holding section 3 is not limited to a single cavity, and it maybe formed into a cavity vessel with the peripheral section closed by etching a sacrificed layer, and in that case, when a sample is put into the sample holding section 3 from its opening, the sample is hardly leaked due to vibration.

Figure 13:
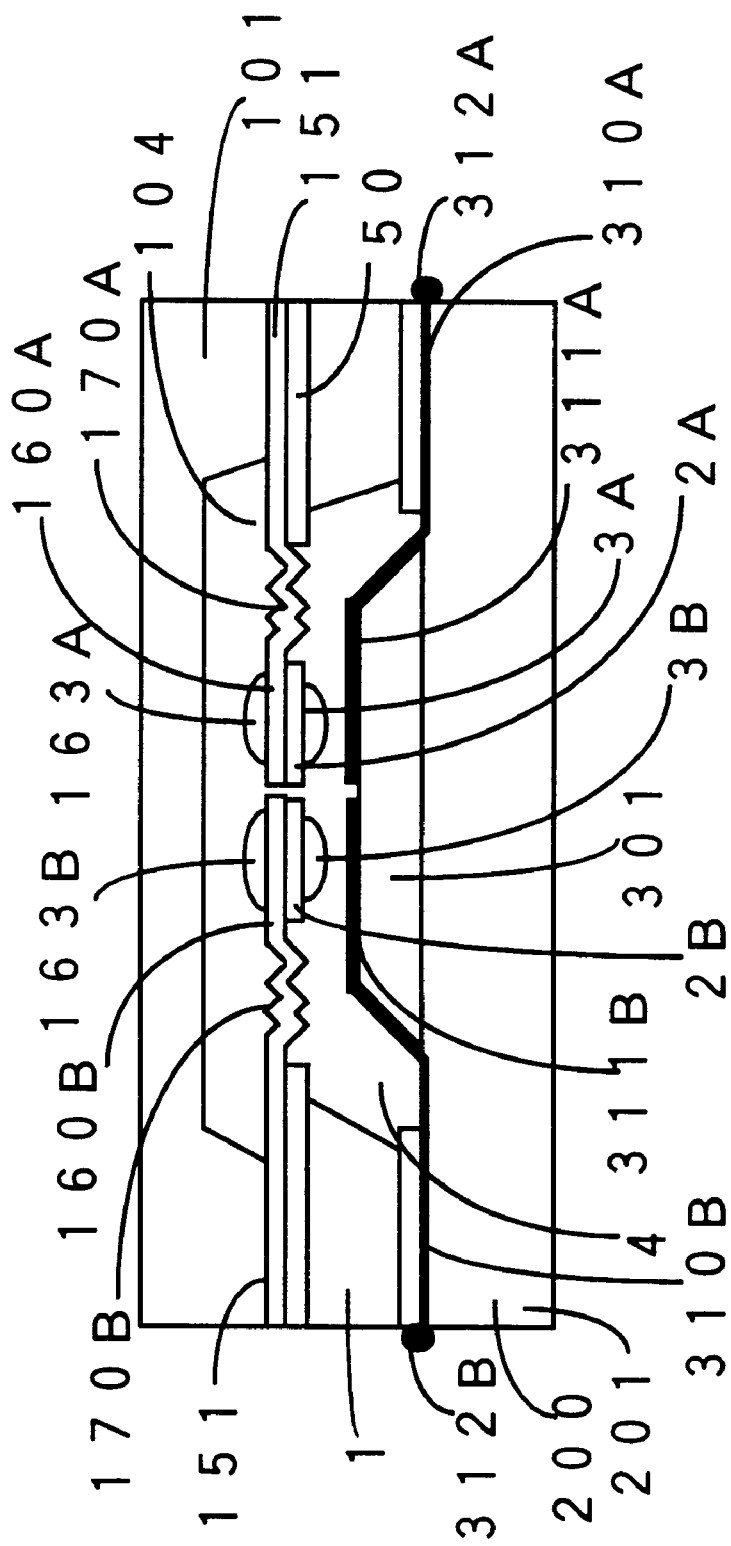
FIG. 13 is a general cross-sectional view showing the embodiment of the basic body of thermal analysis section in the thermal analyzer according to the present invention taken along the line P—P in FIG. 12.

FIG. 13 shows a cross-section of a basic body of the thermal analysis section the thermal analyzer according to the present invention in the embodiment taken along the line P—P in the embodiment shown in FIG. 12.

Figure 14:
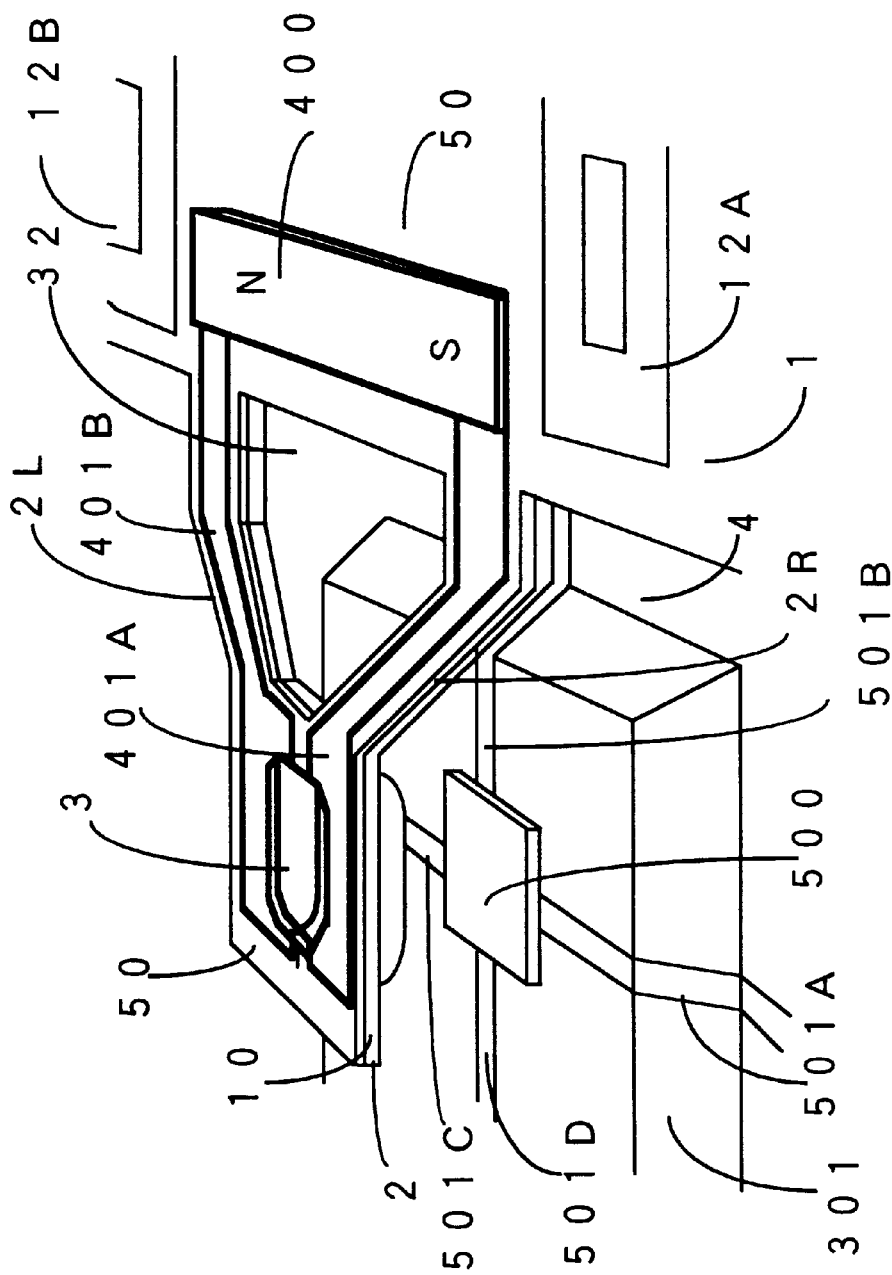
FIG. 14 is a general view showing one embodiment of a basic body of thermal analysis section in the thermal analyzer according to the present invention in a case where the structure is adapted to study of magnetic characteristics of a sample.

FIG. 14 is a general block diagram especially showing a basic body of a thermal analysis section of the thermal analyzer according to the present invention where a measuring unit for measuring a magnetized rate of a magnetic sample or change of the magnetized rate at a transmission point when scanning temperature in order to detect magnetic characteristics of a sample, the thermal analysis section based on a construction similar to that in the embodiment shown in FIG. 12. It should be noted that such component as the temperature detecting unit or self-excited vibrating unit are not shown herein to evade complexity.

In this embodiment, in the measuring unit for measuring a magnetized rate of a magnetic sample or change in the magnetized rate, a permanent magnet such as a samarium cobalt magnetic thin-film with the thickness of around 2 μm is formed as a magnet 400 on the basic board 1, and a sample in the sample holding section 3 is magnetized via magnetic thin-film cores 401A, 401B such as a permalloy also having a thickness of around 2 μm formed via an electrical insulating film 50 on arms of the thin-film heaters 2R, 2L.

In this step, when the magnetic thin-film cores 401A, 401B are extended into inside of a cavity of the sample holding section 3, magnetization can efficiently be executed and a magnetic circuit can easily be formed, so that, even when the magnetic sample reaches the Curie point and becomes a magnetic body, the magnetic poles are generated between the two magnetic thin-film cores 401A, 401B in a cavity of the sample holding section 3 and magnetism can be detected with high sensitivity with a hole element as a magnetism detecting element 500 provided in the lower section thereof. Also wirings 501A, 501B, 501C, and 501D from the hole element as the magnetism detecting element 500 are extended to outside of the chip through a junction face between the substrates as described above. It should be noted that the sample holding section 3 can be vibrated likely in a case described above also by providing electrodes for electrostatic capacity around the magnetism detecting element 500, and also that excited vibration may be generated by making use of expansion and construction by means of cyclically heating the arms of the thin-film heaters 2R, 2L.

Although a permanent magnet comprising a thin-film as a magnet 400 is used for magnetizing a sample in this embodiment, a magnetic thin-film core 401 may be provided at this place for a permanent magnet with thin-film coil for magnetization wound around the magnetic thin-film 401 to form a so-called electric magnet. Also a permanent magnet or an electric magnet may be provided just above the sample holding section 3 on the cover 100. Also a diode, a transistor, or an MR element for detecting magnetism may be used or a search coil may be provided as the magnetism detecting element 500.

Figure 15:
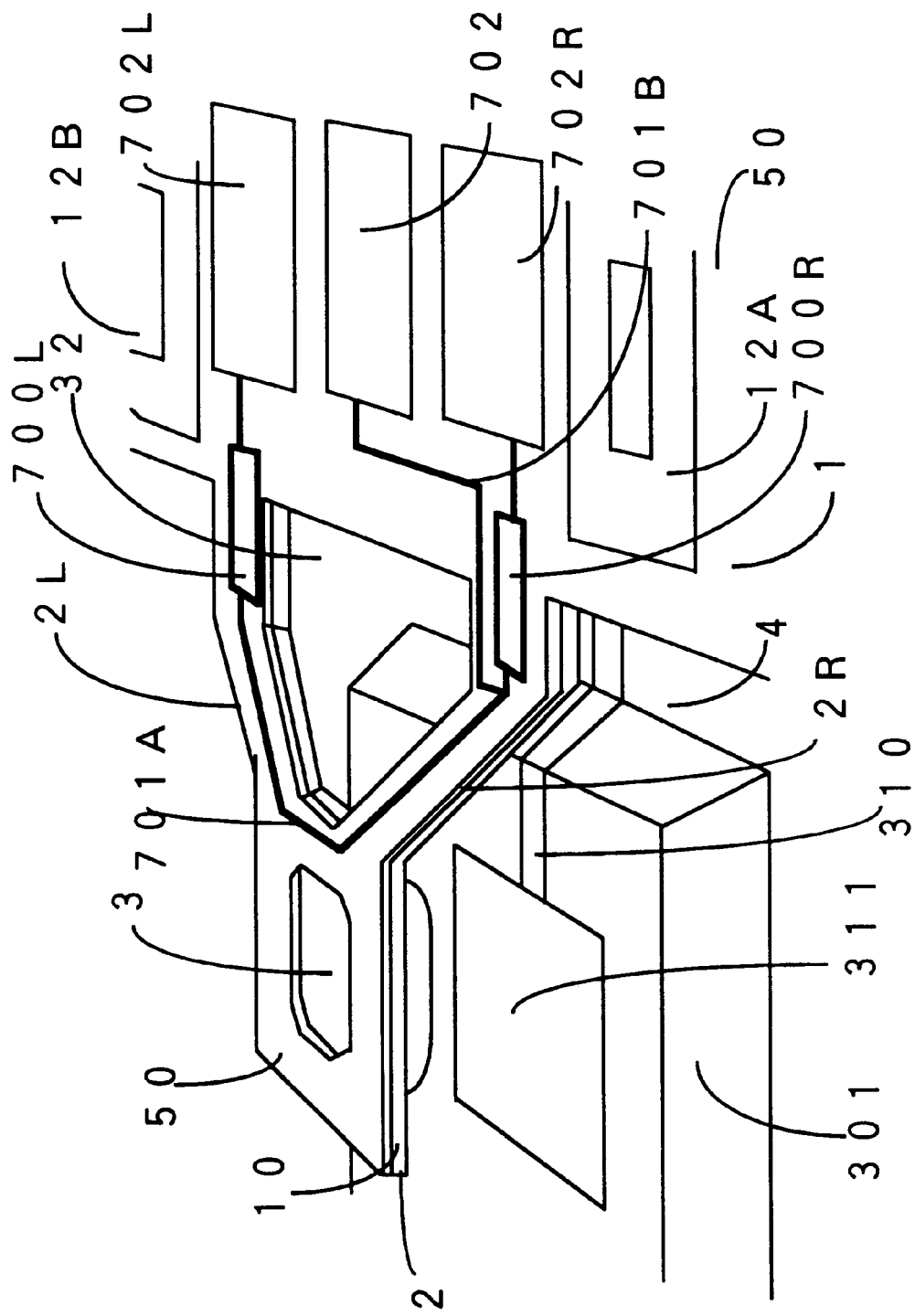
FIG. 15 is a general view showing one embodiment of a basic body of thermal analysis section in the thermal analyzer according to the present invention, said embodiment comprising an electrostatic capacity type of exciting vibration unit in a vibrating section with a canti-lever type of sample holding section and a vibration detecting unit having a piezoelectric element.

FIG. 15 shows an exciting unit and a vibration detecting unit in a vibrating section having a canti-lever formed sample holding section 3 in a basic body of the thermal analysis section of the thermal analyzer according to the present invention, and is a general block diagram showing a case where excitation is generated by making use of an electrostatic sucking force of the AD voltage loaded to a section between the electrode 311 for electrostatic capacity and the impurity diffusion layer 10 as the thin-film heater 2 formed on a substrate 301 with at least a surface thereof electrically insulated, and detection of vibration is executed by, for instance, P-type polysilicon piezo-resistance elements 700R, 700L formed on the electric insulating thin-film 50 on arms of the thin-film heaters 2R, 2L. Also in this figure, many components other than the exciting unit and vibration detecting unit are omitted.

It should be noted that electrodes 702R, 702L of the piezo-resistance element are drawn from the two piezo-resistance elements 700R, 700L, while the electrode 702 is drawn from wiring 701A located between the piezo-resistance elements 700R, 700L via the wiring 701B, and is extended up to outside of the chip like the wiring 310.

Figure 16:
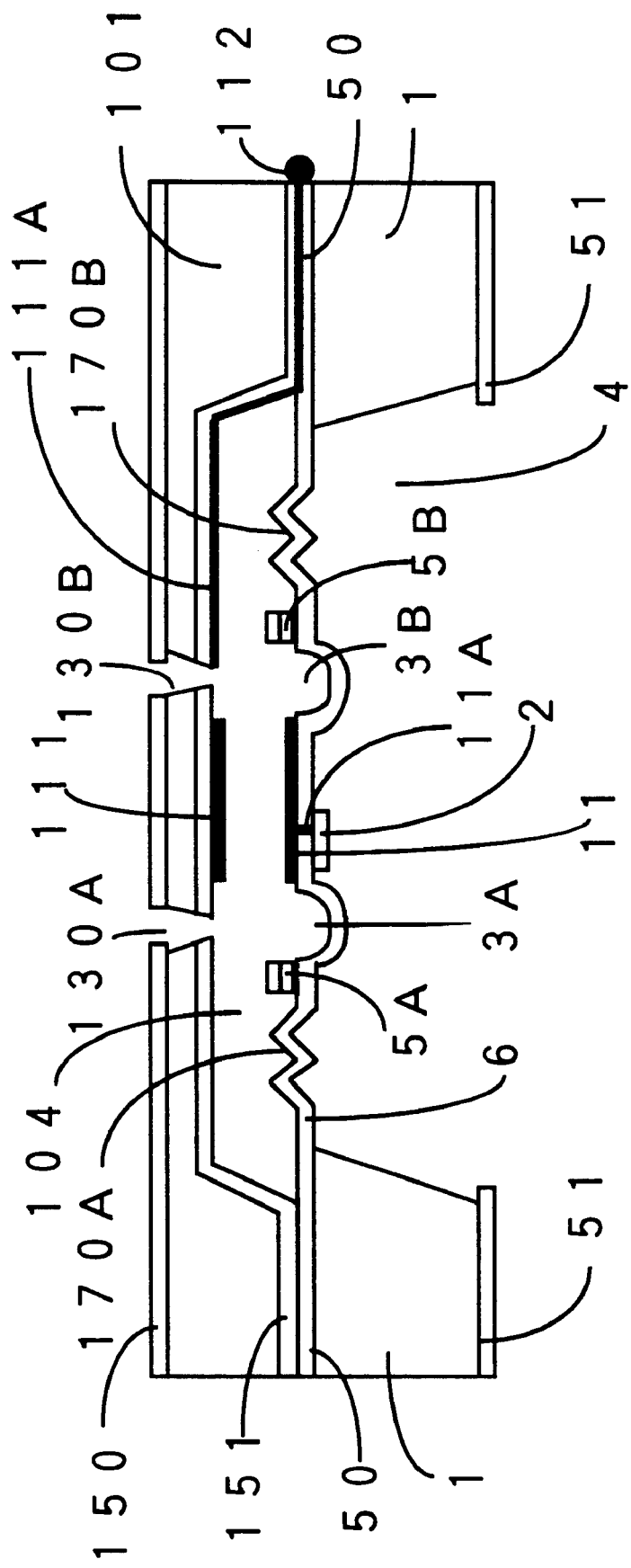
FIG. 16 is a general cross-section showing one embodiment of the present invention in which a thin-film holding section of a basic body of thermal analysis section in the thermal analyzer according to the present invention is implemented as a diaphragm type or as a bridged-structure type and an electrostatic capacity is used by the exciting vibration unit as well as by the vibration detecting unit.

FIG. 16 is a general cross-sectional view showing one embodiment of the thermal analyzer according to the present invention in which the thin-film supporting section 6 of the thermal analysis section is implemented in a diaphragm form or a in a bridged construction form, and shows a case where holes 130A, 130B are provided on the substrate 201 of the cover 200 facing the two sample holding sections 3A, 3B, so that the thin-film supporting section 6 having the sample holding sections 3A, 3B shown in the embodiment in FIG. 7 can easily vibrate.

It should be noted that irregular thin-film springs 170A, 170B are provided in the substrate side of the thin-film supporting section 6 so that the thin-film supporting section 6 can easily vibrate. When the thin-film supporting section 6 has a form like a diaphragm, the thin-film spring 170A and thin-film spring 170B are connected to each other and completely surround the substrate edge.

To realize an exciting unit making use of an electrostatic sucking force caused by an electrostatic capacity, provided are an electrode 111 formed at the bottom 104 of the substrate 210 of the cover 200 and an electrode 11 formed between the sample holding sections 3A, 3B of the thin-film holding section 6 and opposing to the electrode 111. Wiring 111A from the electrode 111 are drawn to outside of the chip and is connected to a terminal 112, while the wiring 11A from the electrode 11 is connected to the thin-film heater 2.

Figure 17:
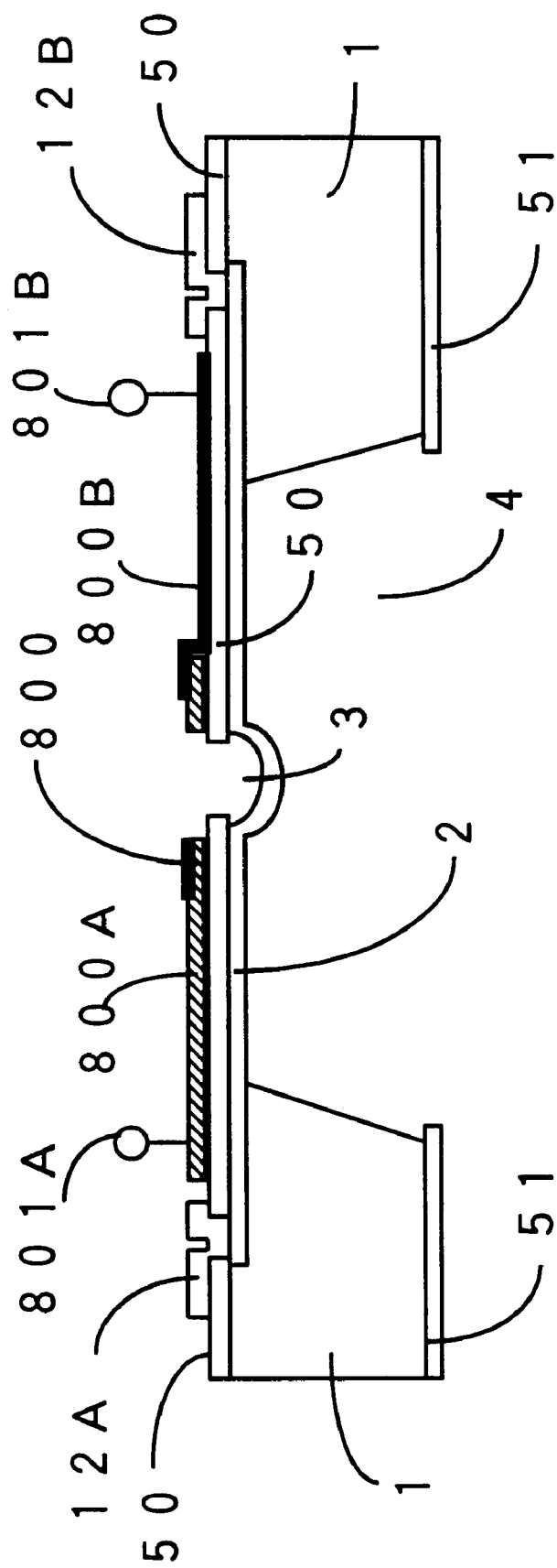
FIG. 17 is a general cross-sectional view showing an area around the thin-film heater in a case where a thin-film Peltie element is formed so that a sample holding section of a basic body of thermal analysis section in the thermal analyzer according to the present invention can not only be heated, but also can be cooled.

FIG. 17 is a general cross-sectional view showing an area close to the thin-film heater 2 in a case where a thin-film Peltie element 800 is formed so that the sample holding section 3 in the thermal analysis section of the thermal analyzer according to the present invention can not only be heated but also cooled, and other components are not shown in the figure.

In this embodiment, a thin-film Peltie element 8 is formed via the electric insulating film 50 on the thin-film heater 2 by depositing, for instance, a BiSbTe thin-film as a P-type thermoelectric material thin-film 800A and a BiTeSe thin-film as an n-type thermoelectric material thin-film 800B up to a thickness of 5 μm respectively by means of sputtering and processing the thin-films with heat. By letting flow a DC current controlled by a temperature controlling circuit provided outside via terminals 801A, 801B to this thin-film Peltie element 800, an area near the sample holding section 3 is cooled to a desired degree below the room temperature and temperature scanning is executed from a temperature below the room temperature. Of course, a current is let flow to the thin-film heater 2 to raise the temperature, but the thin-film Peltie element 800 may simultaneously be driven to easily control temperature.

Figure 18:
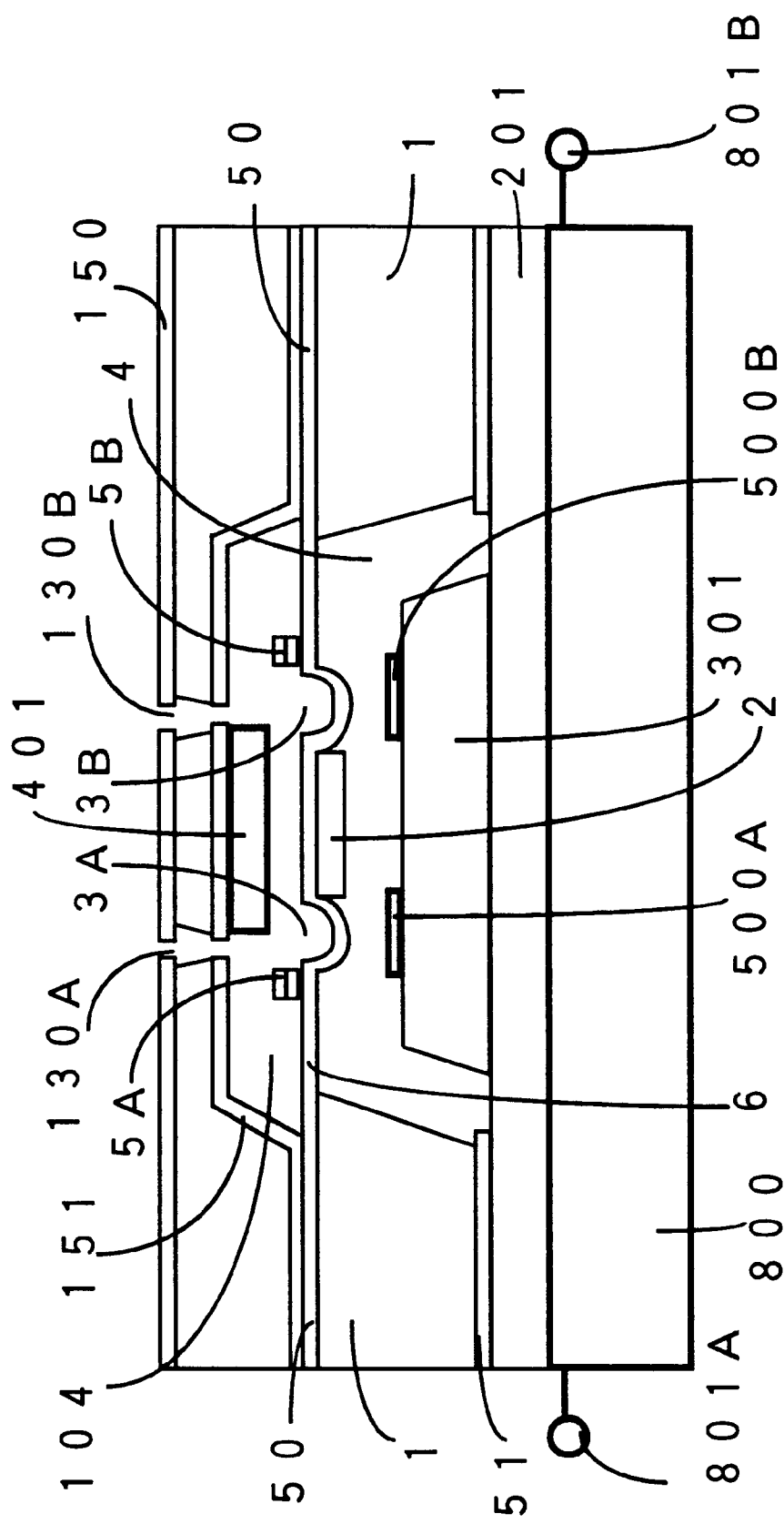
FIG. 18 is a general cross-sectional view showing one embodiment in a case where a Peltie element us attached to a substrate in a basic body of thermal analysis section of the thermal analyzer according to the present invention and in a case where a structure of the thermal analyzer according to the present invention is adapted to measurement of temperature dependency of magnetic characteristics of a sample.

FIG. 18 is a general cross-sectional view showing one embodiment of a thermal analysis section of the thermal analyzer according to the present invention in a case where the Peltie element 800 is attached to the substrate 201 to cool a sample and in a case where the structure is adapted to measurement of dependency on temperature of magnetic characteristics of a sample. Preferably metal such as copper having high heat conductivity may be used as a material for the substrate 201. This substrate 201 and the Peltie element 800 are thermally connected to each other. A DC current flows to the Peltie element 800 through the terminals 801A, 801B thereof, and the temperature is adjusted to a desired degree by a temperature control circuit provided externally.

Construction in this embodiment is similar to that shown in FIG. 16, but in this case excitation is not made, and also temperature of the sample holding sections 3A, 3B changes similarly to that of the thin-film heater 2. Also herein, components such as the electrode are not shown to evade complexity.

In this embodiment, a sample is magnetized by a magnet 400 such as a permanent magnet or an electric magnet formed on the bottom of the cavity section 104 provided in the substrate 201 of the cover 200 in vicinity to and a equal space from the two sample holding sections 3A, 3B (It is needless to say that, if the sample is not a magnetic body at the temperature, the sample is not magnetized), and a magnetized rate of the sample or change in the magnetized rate is detected with magnetism detecting elements 500A, 500B such as hole elements provided in vicinity to lower sections of the two sample holding sections 3A, 3B respectively. The two sample holding sections 3A, 3B with a standard sample and a sample to be measured put in respectively can differentially be operated to improve the sensitivity.

Although not described in relation to this embodiment, it is needless to say that the thin-film springs 170A, 170B are formed as shown in FIG. 16 and excited by making use of an electrostatic capacity to make the thin-film springs 170A, 170B function like a VSM.

In the embodiment described above, an electrostatic capacity type of electrostatic sucking force is used as an exciting unit, and also expansion and contraction of a thin-film heater are made use of for the same purpose, but excitation can be generated by using a piezo-electric thin-film such as a PZT or a ZnO thin-film. Of course this piezo-electric thin-film can also be used as a vibration detecting unit.

The embodiments of the present invention described above are provided only as examples, and various combinations of the embodiments described above are possible, and in addition various modifications of the prevent invention are possible without changing the gist, actions, and effects of the present invention.

Although not described in the embodiments above, the thermal analyzer according to the present invention can be made detachable to and from a connected provided externally by changing a form and a position of each electrode and extending it up to an upper surface of the thermal analysis section, for instance, an upper surface of the cover or extending it to a side face section thereof.

Further, as clearly indicated by the embodiments described above, as the thermal analysis section of the thermal analyzer according to the present invention can be mass-produced as a device based on unified specifications by making use of the minute machining technology for semiconductors, and a basic body of the thermal analysis section can be used as a disposable one.

As described above, the thermal analyzer according to the present invention is a thermal analyzer for scanning temperature by heating or cooling a sample and measuring a thermal change based on physical and chemical changes of the sample as a function of temperature or time comprising: a heat-generating section for heating a sample monolithically formed with a substrate as a thin-film heater with a cavity section in a lower section thereof; a sample holding section for holding the sample; and a temperature detecting section for detecting temperature of the sample holding section; wherein the sample holding section and the temperature detecting section are monolithically formed on the thin-film filter or in an area close to the thin-film heater in a thin-film supporting section for supporting the thin-film heater, so that it is possible to provide a thermal analyzer which enables measurement with an extremely small quantity of sample by heating the sample with a heater having an extremely small heat capacity and also the sample can be heated up to a high temperature with high response speed, and also which can be mass-produced with uniformed specifications.

Further only an extremely small quantity of sample is required for measurement, so that heat transmission in biological substances such as protein or nucleic acid, or thermal transmission of magnetic characteristic or other characteristics in a substance can be measured with high response speed, and also a sample can be heated to a high temperature with a minute electric power, so that a handy thermal analyzer can be realized. Further the heater, sample holding section, and heat detecting section for measuring temperature of the sample holding section are formed monolithically, so that the heat analyzers can be mass-produced based on the uniformed specifications with the minute machining technology for semiconductors. For this reason, it is possible to realize a high precision and low price thermal analyzer.

In the thermal analyzer according to the present invention, a plurality of the sample holding sections and a plurality of temperature detecting section for detecting temperature of the sample holding sections respectively are provided in one thin-film supporting section including the thin-film heater, so that the thermal analyzers can be mass-produced based on the uniformed specifications making use of the minute machining technology for semiconductors.

In the heat analyzer according to the present invention, thermal connection between the thin-film heater and the sample holding sections is adjusted so that temperature of each of the plurality of sample holding section is minutely different from that of other ones, and a minute temperature difference is generated between one sample and the other sample during rising or cooling of temperature of the thin-film heater, that is to say, temperature scanning, and for this reason change of thermal state of the samples can be expressed as a difference in temperature.

In the thermal analyzer according to the present invention, the thermal holding sections are formed with cavities each consisting of a thin-film, so that an extremely small quantity of same can be mounted there for analysis with the response speed improved.

In the thermal analyzer according to the present invention, a substrate having the heat-generating section is made from a mono-crystalline material and a cover for covering the heat-generating section and the sample holding sections is provided therein, so that a form for a thin-film heater or a sample holding section having high precision and high reproducibility can be defined and formed by making use of a difference in etching speed in each face orientation of a crystal.

In the thermal analyzer according to the present invention, holes are provided and positioned on areas of the cover just above the sample holding sections so that samples can be put in through the holes, and for this reason an extremely minute quantity of sample can be put in through the holes into the sample holding section each also have extremely small size.

In the thermal analyzer according to the present invention, a size of each of the holes is set to a specified value and the holes are used as measures for measuring a quantity of a sample, so that a quantity of sample to be measured can easily be decided, which improves the convenience. Especially, when the cover is made from a monocrystaline material, it is possible to obtain high precision hole dimensions with high reproducibility by making use of the etching speed according to a face orientation of the crystal. It should be noted that a minute powder or a liquidous state is preferable as a sample.

In the thermal analyzer according to the present invention, the heat-generating section for heating a sample is provided only on or in vicinity to the sample holding section, so that a power injected into the heat-generating section for heating a sample is effectively added to the sample. In other words, power consumption can be minimized in the thin-film heater other than the thin-film supporting section for a thin-film heater with a small heat capacity or the sample holding section can be minimized.

In the thermal analyzer according to the present invention, a thin-film cover for covering at least the sample holding section during measurement is provided, so that a sample put in the sample holding section can be prevented from spilling. Usually when the sample holding section is vibrated, the sample comes out from the sample holding section, but with the present invention, this phenomenon is suppressed, and the sample is hardly evaporated.

The thermal analyzer according to the present invention further comprises an exciting unit for exciting at least the sample holding section; a vibration detecting unit for detecting vibration of the sample holding section; and an self-excited vibrating unit for self-excited vibration based on a combination of the vibrating unit with the vibrating detecting unit, so that the sample can be vibrated. It should be noted that, to vibrate a sample, it is advantageous to vibrate the sample holding section in self-excitation, and it is more advantageous to use resonance. For this purpose, to cause self-excitation of the sample holding section, at first a exciting unit for excitation and a vibration detecting unit for detecting vibration are combined, and a feed-back system is formed with an amplifier to realize the self-excited vibration unit.

In the thermal analyzer according to the present invention, the exciting unit vibrates and excites the sample holding section making use of expansion and contraction caused by AC current for excitation with a current for heating a sample flowing through the thin-film heater superimposed thereon, so that a micro-heater for excitation is not required to be provided anew, which allows simplification of the configuration.

In the thermal analyzer according to the present invention, the exciting unit excites the sample holding section by making use of an electrostatic sucking force, in other words, an electrostatic capacity is formed as an exciting unit between the thin-film section raised in the air with the sample holding section provided thereon and the substrate or vicinity thereto, and an electrostatic sucking force generated conductive bodies such as electrodes for the electrostatic capacity is made use of, so that a very large force can be generated between conductive bodies provided in vicinity to each other.

In the thermal analyzer according to the present invention, the vibration detecting unit detects vibration by making use of change in piezoelectric resistance, so that vibration can easily be detected.

In the thermal analyzer according to the present invention, the vibration detecting unit detects vibration by making use of change in an electrostatic capacity, so that vibration can easily be detected.

The thermal analyzer according to the present invention further comprises a mass measuring unit for measuring mass of a sample or change in mass of the sample, so that the thermal analyzer can also be used as a calorie meter which can also measure change in calorie by measuring loss of a sample due to evaporation or for other reasons or change in mass of the sample due to a chemical reaction or for other reasons.

The thermal analyzer according to the present invention further comprises a Peltie element as a cooling unit for cooling a sample, so that temperature scanning can be executed by cooling the sample. In other words, when the sample is heated, temperature scanning can be made only above the room temperature, but in this method the sample can be cooled for obtaining various types of data by scanning the sample under a low temperature.

In the thermal analyzer according to the present invention, the cooling unit is positioned on or at a place close to the sample holding section on a thin-film formed on the sample holding section, so that a sample can easily be cooled.

In the thermal analyzer according to the present invention, the cooling unit cools a substrate on which the sample holding section is formed, so that thermal conduction from the substrate or cooling due to the peripheral area or gas can be made use of.

The thermal analyzer according to the present invention further comprises a magnetized rate measuring unit for measuring a magnetized rate of a sample or change in a magnetized rate thereof, so that thermal properties of a magnetic sample can be clarified.

In the thermal analyzer according to the present invention, the magnetized rate measuring unit magnetizes a sample using a magnet monolithically formed on a substrate, in other words, magnetization of a sample is executed by a permanent magnet or an electric magnet, and the magnet and the substrate are monolithically formed and provided in vicinity to a sample, so that the sample can be magnetized with a small size magnet.

In the thermal analyzer according to the present invention, the magnetized rate measuring unit detects a magnetized rate of a sample or change in the magnetized rate thereof using a magnetism detecting element monolithically formed on a substrate, in other words a magnetized rate of sample or change in the magnetized rate is detected with a magnetism detecting element such as a hole element, an MR element, a diode or a transistor for detecting magnetism, or a coil type of magnetic head, so that the thermal analyzer can be mass-produced by monolithically forming the magnetism detecting element and the substrate and providing them in vicinity to each other, and also with the thermal analyzer magnetism can be detected with high sensibility.

The thermal analyzer according to the present invention further comprises an exciting unit for exciting at least the sample holding section; a vibration detecting unit for detecting vibration of the sample holding section; and a self-excited vibrating unit for self-excited vibration based on a combination of the exciting unit with the vibration detecting unit, so that a magnetized rate of a sample or change in the magnetized rate can be detected by vibrating a sample with the exciting unit, which makes it possible to detect, by making use of the principle of VSM, an extremely small quantity of magnetic sample by using a magnetism detecting element provided in vicinity thereto with high sensitivity In the measuring method with a thermal analyzer according to the present invention, when temperature scanning is executed with the thermal analyzer by letting a current flow through a thin-film heater, a current component for heating or cooling a sample at a constant rate is superimposed over an AD current component for minutely changing temperature, and a temperature change component corresponding to the AD current component is taken out as a signal from the temperature detecting unit; and the signal is subjected to a prespecified processing, and for that purpose the thermal analyzer according to the above invention has a high responsibility, so that a current component for heating or cooling a sample at a constant rate can be superimposed over an AD current component for minutely changing temperature. In other words, the measuring method with a thermal analyzer having a high responsibility even at a minute power can be provided.

In the measuring method with a thermal analyzer according to the present invention, by using the thermal analyzer according to the present invention, a standard sample is put in at least one sample holding section among the plurality of sample holding sections; a sample to be measured is put in other sample holding sections; and thermal characteristics of the sample to be measured is measured according to information concerning difference in temperature between the standard sample and the sample to be measured by scanning temperature of the two types of sample, so that it is possible to provide a measuring method with a thermal analyzer which can measure with high responsibility even at a minute power.

In the measuring method according to the present invention, the standard sample and the sample to be measured are heated by different thin-film heaters to eliminate difference in temperature between the two types of sample, so that it is possible to obtain not only temperature information such as a melting point of a sample, but also information concerning the latent heat or evaporation. It should be noted herein that the different thin-film heaters may be provided on a thin-film heater supporting section of one piece of thin-film heater, or formed on one substrate but on independent thin-film supporting sections respectively. It is needless to say that the different thin-film heaters may be provided on one substrate but directly on independent thin-film heaters respectively.

In the measuring method with a thermal analyzer according to the present invention, the same sample to be measured is put in a plurality of sample holding sections; temperature is scanned for the samples; and the thermal characteristics of the sample to be measured is measured according to information concerning a difference in temperature between the same samples, so that it is possible to provide a measuring method with a thermal analyzer which can measure with high responsibility at a minute power.

In the measuring method with a thermal analyzer according to the present invention, at least the sample holding section is vibrated in excitation, and mass of a sample is measured from a resonance frequency at the point of time and also change in mass thereof is measured from shift of the resonance frequency, so that mass of the sample can be measured, by exciting the sample holding section, from a resonance frequency at that point of time and also change in mass thereof can be measured from shift of the resonance frequency.

Further in the measuring method with a thermal analyzer according to the present invention, the same sample to be measured is put in a plurality of sample holding sections and temperature scanning is executed all together, but when no sample is put in (when the sample holding section is kept empty), a minute difference in temperature is generated between different sample holding sections, and the thermal characteristics of the sample to be measured is measured according to information on the temperature difference between the same samples, so that the information concerning the temperature difference between the same samples to be measured in different sample holding sections indicates a difference in temperature, which is equivalent to expression of differential value concerning temperature in temperature scanning at a constant speed.

Further with the measuring method according to the present invention, especially by making use of the possibility of high speed response at a minute power, it becomes possible to generate minute change in temperature for executing temperature scanning by superimposing a minute AD current with a frequency of several hertz on a current for heating a thin-film heater, to form a sample holding section at a position extremely close to the same thin-film heater, to finely adjust the temperature difference between the sample holding sections by minutely adjusting a range of each sample holding section from the thin-film heater, and further to put the same sample in two sample holding sections for measuring a temperature difference between the sample holding sections, and to detect mass or change in mass of a sample by vibrating the sample, so that the thermal analyzer can also be used as a calorie meter for measuring a heating value. Also it is possible to measure thermal characteristics of an extremely small quantity of substance, and thus the measuring method for thermal analysis which has been impossible in the thermal analyzer according to the conventional technology can easily be achieved.

This application is based on Japanese patent applications No. HEI 9-007070 and No. HEI 9-034077 filed in the Japanese Patent Office on Jan. 17, 1997 and Feb. 18, 1997, respectively, the entire contents of which are hereby incorporated by reference.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A thermal analyzer for scanning temperature by thermally altering a sample and measuring a thermal change based on physical and chemical changes of said sample as a function of at least one of temperature and time comprising:
   a monolithic heat-generating section configured to heat a sample, said monolithic heat-generating section being monolithically formed on a substrate and including
   a thin-film heater, and
   a cavity section, said cavity section being formed in a lower section of the thin-film heater and forming a sample holding section configured to hold said sample; and a temperature detecting section configured to detect a temperature of said sample holding section;

wherein said sample holding section and said temperature detecting section are monolithic and are formed on said thin-film heater.

2. A thermal analyzer according to claim 1; further comprising:

additional sample holding sections; and additional temperature detecting sections for detecting temperatures of said additional sample holding sections, respectively, said additional sample holding sections and temperature detecting sections being monolithically formed and provided in one of the thin-film holding sections including said thin-film heater.

3. A thermal analyzer according to claim 2; wherein a thermal connection between said thin-film heater and said additional sample holding sections is adjusted so that respective temperatures of each of said additional sample holding sections are minutely different from one another.

4. A thermal analyzer according to claim 1; wherein said sample holding section is formed with cavities, each of said cavities consisting of a thin-film.

5. A thermal analyzer according to claim 1; wherein the substrate is made from a mono-crystalline material and a cover for covering said heat-generating section and said sample holding sections is provided therein.

6. A thermal analyzer according to claim 5; wherein holes are provided and positioned on areas of said cover just above said sample holding sections so that samples can be put in through said holes.

7. A thermal analyzer according to claim 6; wherein a size of each of said holes is set to a specified value and said holes are used as measures for measuring a quantity of a sample.

8. A thermal analyzer according to claim 1 further comprising a thin-film cover for covering said sample holding section during measurement.

9. A thermal analyzer for scanning temperature by thermally altering a sample and measuring a thermal change based on physical and chemical changes of said sample as a function of at least one of temperature and time comprising:

a heat-generating section for heating a sample, including a thin-film heater with a cavity section in a lower section thereof;

a sample holding section for holding said sample;

a temperature detecting section for detecting a temperature of said sample holding section; wherein said sample holding section and said temperature detecting section are monolithically formed on one of said thin-film heater and an area proximate said thin-film heater in a thin-film supporting section for supporting said thin-film heater;

an exciting unit for exciting said sample holding section;

a vibration detecting unit for detecting vibration of said sample holding section; and an self-excited vibrating unit for causing vibration based on a cooperation of said vibrating unit with said vibration detecting unit.

10. A thermal analyzer according to claim 9, wherein said exciting unit excites said sample holding section by expansion and contraction of the exciting unit caused by application of an AC current to the exciting unit.

11. A thermal analyzer according to claim 9; wherein said exciting unit excites said sample holding section by making use of an electrostatic sucking force.

12. A thermal analyzer according to claim 9; wherein said vibration detecting unit detects vibration by making use of a change in piezoelectric resistance.

13. A thermal analyzer according to claim 9; wherein said vibration detecting unit detects vibration by making use of a change in an electrostatic capacity.

14. A thermal analyzer according to claim 1 further comprising a mass measuring unit for measuring a mass of the sample.

15. A thermal analyzer according to claim 1 further comprising a Peltier element as a cooling unit for cooling the sample.

16. A thermal analyzer according to claim 15, wherein said cooling unit is proximate said sample holding section.

17. A thermal analyzer according to claim 15; wherein said cooling unit cools the substrate on which said sample holding section is formed.

18. A thermal analyzer according to claim 1 further comprising a magnetized rate measuring unit for measuring a magnetized rate of a sample.

19. A thermal analyzer according to claim 18; wherein said magnetized rate measuring unit magnetizes a sample using a magnet monolithically formed on the substrate.

20. A thermal analyzer according to claim 18, wherein said magnetized rate measuring unit detects the magnetized rate of the sample using a magnetism detecting element monolithically formed on the substrate.

21. A thermal analyzer according to claim 18 further comprising:

an exciting unit for exciting said sample holding section;

a vibration detecting unit for detecting vibration of said sample holding section; and a self-excited vibrating unit for self-excited vibration based on a cooperation of said exciting unit with said vibration detecting unit.

22. A method of measuring with a thermal analyzer for scanning temperature by thermally altering a sample and measuring a thermal change based on physical and chemical changes of said sample as a function of at least one of temperature and time, said thermal analyzer including a heat-generating section for heating a sample monolithically formed with a substrate as a thin-film heater with a cavity section in a lower section thereof, a sample holding section for holding said sample, and a temperature detecting section for detecting a temperature of said sample holding section; wherein said sample holding section and said temperature detecting section are monolithically formed on one of said thin-film heater and an area proximate said thin-film heater in a thin-film supporting section for supporting said thin-film heater, comprising the steps of:

superimposing a current component for thermally altering a sample at a constant rate over an AC current component for minutely changing temperature; and generating and processing a temperature change component corresponding to said AC current component as a signal from a temperature detecting unit.

23. A method for measuring with a thermal analyzer for scanning temperature by thermally altering a sample and measuring a thermal change based on physical and chemical changes of said sample as a function of at least one of temperature and time, said thermal analyzer comprising a heat-generating section for heating a sample monolithically formed with a substrate as a thin-film heater with a cavity section in a lower section thereof, a first sample holding section for holding said sample, a first temperature detecting section for detecting temperature of said first sample holding section; wherein said sample holding section and said temperature detecting section are monolithically formed on one of said thin-film heater and an area proximate said thin-film heater in a thin-film supporting section for supporting said thin-film heater, and a second sample holding section and a second temperature detecting section for detecting a temperature of said second sample holding section provided in one of the thin-film holding sections including said thin-film heater, comprising the steps of:

putting a standard sample in said first sample holding section;

putting a sample to be measured in the second sample holding section; and measuring the thermal characteristics of said sample to be measured according to information corresponding to a difference in temperature between the standard sample and said sample to be measured by scanning the respective temperatures of the standard sample and the sample to be measured.

24. A method according to claim 23, wherein the thermal analyzer comprises a heating system in which said standard sample and said sample to be measured are heated by different thin-film heaters to minimize a difference in temperature between the standard sample and the sample to be measured.

25. A method of measuring with a thermal analyzer for scanning temperature by thermally altering a sample and measuring a thermal change based on physical and chemical changes of said sample as a function of at least one of temperature and time, said thermal analyzer comprising a heat-generating section for heating a sample monolithically formed with a substrate as a thin-film heater with a cavity section in a lower section thereof, a first sample holding section for holding said sample, a first temperature detecting section for detecting a temperature of said first sample holding section; wherein said first sample holding section and said first temperature detecting section are monolithically formed on one of said thin-film heater and an area proximate said thin-film heater in a thin-film supporting section for supporting said thin-film heater, a second sample holding section and a second temperature detecting section for detecting a temperature of said second sample holding section provided in one of the thin-film holding sections including said thin-film heater, and a thermal connection between said thin-film heater and said sample holding sections adjusted so that the temperature of the first sample holding section is minutely different from the temperature of the second sample holding section, comprising the steps of:

putting first and second samples in respective of said first and second sample holding sections, said first and second samples being identical;

scanning temperature of the first and second samples; and measuring thermal characteristics of the first sample according to information corresponding to a difference in temperature between the first and second samples.

26. A method of measuring with a thermal analyzer for scanning temperature by thermally altering a sample and measuring a thermal change based on physical and chemical changes of said sample as a function of at least one of temperature and time, said thermal analyzer including a heat-generating section for heating a sample monolithically formed with a substrate as a thin-film heater with a cavity section in a lower section thereof, a sample holding section for holding said sample, a temperature detecting section for detecting a temperature of said sample holding section, an exciting unit for exciting said sample holding section, a vibration detecting unit for detecting vibration of said sample holding section, and a self-excited vibrating unit for causing vibration based on a cooperation of said vibrating unit with said vibration detecting unit; wherein said sample holding section and said temperature detecting section are monolithically formed on one of said thin-film heater and an area proximate said thin-film heater in a thin-film supporting section for supporting said thin-film heater, comprising the steps of:

exciting vibration of at least the sample holding section; and measuring a mass of a sample based on a shift of a resonance frequency applied to the sample.

27. A method of measuring with a thermal analyzer for scanning temperature by thermally altering a sample and measuring a thermal change based on physical and chemical changes of said sample as a function of at least one of temperature and time, said thermal analyzer including a heat-generating section for heating a sample monolithically formed with a substrate as a thin-film heater with a cavity section in a lower section thereof, a sample molding section for holding said sample, a temperature detecting section for detecting a temperature of said sample holding section, and a mass measuring unit for measuring at least one of a mass of a sample and a change in mass of the sample; wherein said sample holding section and said temperature detecting section are monolithically formed on one of said thin-film heater and an area proximate said thin-film heater in a thin-film supporting section for supporting said thin-film heater, comprising the steps of:

exciting the vibration of the sample holding section; and measuring a mass of a sample based on a shift of a resonance frequency applied to the sample.

* * * * *